United States Patent
Golec et al.

(12)

(10) Patent No.: US 6,350,741 B1
(45) Date of Patent: Feb. 26, 2002

(54) INHIBITORS OF INTERLEUKIN-1β CONVERTING ENZYME

(75) Inventors: Julian M. C. Golec, Swindon (GB); David J. Lauffer, Stow, MA (US); David J. Livingston, Lawrenceville, NJ (US); Michael D. Mullican, Needham, MA (US); Philip L. Nyce, Millbury, MA (US); Andrea L. C. Robidoux, Andover, MA (US); Marion W. Wannamaker, Stow, MA (US)

(73) Assignee: Vertex Pharmaceutical, Inc., Cambridge, MA (US)

( * ) Notice: Subject to any disclaimer, the term of this patent is extended or adjusted under 35 U.S.C. 154(b) by 0 days.

(21) Appl. No.: 09/326,494

(22) Filed: Jun. 4, 1999

Related U.S. Application Data

(63) Continuation of application No. PCT/US97/22355, filed on Dec. 5, 1997.
(60) Provisional application No. 60/050,796, filed on Jun. 26, 1997, provisional application No. 60/041,938, filed on Apr. 4, 1997, and provisional application No. 60/032,129, filed on Dec. 6, 1996.

(51) Int. Cl.[7] ..................... A61K 31/55; C07D 487/00; C07D 223/16
(52) U.S. Cl. ....................................... 514/213; 540/523
(58) Field of Search ........................... 540/523; 514/213

(56) References Cited

U.S. PATENT DOCUMENTS

| | | | | |
|---|---|---|---|---|
| 5,580,979 A | * | 12/1996 | Bachovchin | 540/509 |
| 5,843,941 A | * | 12/1998 | Marsters, Jr. et al. | 514/221 |

FOREIGN PATENT DOCUMENTS

| | | | |
|---|---|---|---|
| JP | 09 295 996 A | 11/1997 | ........... C07K/5/023 |
| WO | WO 95/35308 | 12/1995 | ........... C07K/5/023 |
| WO | WO 97/22619 | 6/1997 | ............ C07K/5/02 |

OTHER PUBLICATIONS

R.E. Dolle et al, "Pyridazinodiazepines As a High–Affinity, $P_2$–$P_3$ Peptidomimetic Class of Interleukin–1β–Converting Enzyme Inhibitor", *Journal of Medicinal Chemistry*, 40(13) (1997).
AN 98–046961, Derwent WPI, File 351, JP 09 295 996 A Abstract.

* cited by examiner

*Primary Examiner*—Bruck Kifle
(74) *Attorney, Agent, or Firm*—Fish & Neave; James F. Haley, Jr.; Kristin M. Joslyn

(57) ABSTRACT

The present invention relates to novel classes of compounds which are inhibitors of interleukin-1β converting enzyme ("ICE"). This invention also relates to pharmaceutical compositions comprising these compounds. The compounds and pharmaceutical compositions of this invention are particularly well suited for inhibiting ICE activity and consequently, may be advantageously used as agents against interleukin-1-("IL-1"), apoptosis-, interferon-γ inducing factor-(IGIF), or interferon-γ-("IFN-γ") mediated diseases, including inflammatory diseases, autoimmune diseases, destructive bone disorders, proliferative disorders, infectious diseases, and degenerative diseases. This invention also relates to methods for inhibiting ICE activity and decreasing IGIF production and IFN-γ production and methods for treating interleukin-1, apoptosis- and interferon-γ-mediated diseases using the compounds and compositions of this invention. This invention also relates to methods of preparing the compounds of this invention.

18 Claims, No Drawings

INHIBITORS OF INTERLEUKIN-1β CONVERTING ENZYME

CROSS-REFERENCE TO RELATED APPLICATIONS

This application is a continuing application of co-pending International patent application PCT/US97/22355, filed Dec. 5, 1997, which claims priority from United States provisional patent application No. 60/050,796, filed Jun. 26, 1997, which is a continuation-in-part of U.S. provisional patent application No. 60/041,938, filed Apr. 4, 1997, which is a continuation-in-part of U.S. provisional patent application No. 60/032,129, filed Dec. 6, 1996.

TECHNICAL FIELD OF THE INVENTION

The present invention relates to novel classes of compounds which are inhibitors of interleukin-1β converting enzyme ("ICE"). This invention also relates to pharmaceutical compositions comprising these compounds. The compounds and pharmaceutical compositions of this invention are particularly well suited for inhibiting ICE activity and consequently, may be advantageously used as agent- against interleukin-1-("IL-1"), apoptosis-, interferon-γ inducing factor-(IGIF), or interferon-γ-("IFN-γ") mediated diseases, including inflammatory diseases, autoimmune diseases, destructive bone disorders, proliferative disorders, infectious diseases, and degenerative diseases. This invention also relates to methods for inhibiting ICE activity and decreasing IGIF production and IFN-γ production and methods for treating interleukin-1, apoptosis- and interferon-γ-mediated diseases using the compounds and compositions of this invention. This invention also relates to methods of preparing the compounds of this invention.

BACKGROUND OF THE INVENTION

Interleukin 1 ("IL-1") is a major pro-inflammatory and immunoregulatory protein that stimulates fibroblast differentiation and proliferation, the production of prostaglandins, collagenase and phospholipase by synovial cells and chondrocytes, basophil and eosinophil degranulation and neutrophil activation. Oppenheim, J. H. et al., *Immunology Today*, 7, pp. 45–56 (1986). As such, it is involved in the pathogenesis of chronic and acute inflammatory and autoimmune diseases. For example, in rheumatoid arthritis, IL-1 is both a mediator of inflammatory symptoms and of the destruction of the cartilage proteoglycan in afflicted joints. Wood, D. D. et al., *Arthritis Rheum.* 26, p. 975, (1983); Pettipher, E. J. et al., *Proc. Natl. Acad. Sci. USA* 71, p. 295 (1986); Arend, W. P. and Dayer, J. M., *Arthritis Rheum.* 38, p. 151 (1995). IL-1 is also a highly potent bone resorption agent. Jandiski, J. J., *J. Oral Path.* 17, p. 145 (1988); Dewhirst, F. E. et al., *J. Immunol.* 8, p. 2562 (1985). It is alternately referred to as "osteoclast activating factor" in destructive bone diseases such as osteoarthritis and multiple myeloma. Bataille, R. et al., *Int. J. Clin. Lab. Res.* 21(4), p. 283 (1992). In certain proliferative disorders, such as acute myelogenous leukemia and multiple myeloma, IL-1 can promote tumor cell growth and adhesion. Bani, M. R., *J. Natl. Cancer Inst.* 83, p. 123 (1991); Vidal-Vanaclocha, F., *Cancer Res.* 54, p. 2667 (1994). In these disorders, IL-1, also stimulates production of other cytokines such as IL-6, which can modulate tumor development (Tartour et al., *Cancer Res.* 54, p. 6243 (1994). IL-1 is predominantly produced by peripheral blood monocytes as part of the inflammatory response and exists in two distinct agonist forms, IL-1α and IL-1β. Mosely, B. S. et al., *Proc. Nat. Acad. Sci.*, 84, pp. 4572–4576 (1987); Lonnemann, G. et al., *Eur. J. Immunol.*, 19, pp. 1531–1536 (1989).

IL-1β is synthesized as a biologically inactive precursor, pIL-1β. pIL-1β lacks a conventional leader sequence and is not processed by a signal peptidase. March, C. J., *Nature*, 315, pp. 641–647 (1985). Instead, pIL-1β is cleaved by interleukin-1β converting enzyme ("ICE") between Asp-116 and Ala-117 to produce the biologically active C-terminal fragment found in human serum and synovial fluid. Sleath, P. R. et al., *J. Biol. Chem.*, 265, pp. 14526–14528 (1992); Howard, A. D. et al., *J. Immunol.*, 147, pp. 2964–2969 (1991). ICE is a cysteine protease localized primarily in monocytes. It converts precursor IL-1β to the mature form. Black, R. A. et al., *FEBS Lett.*, 247, pp. 386–390 (1989); Kostura, M. J. et al., *Proc. Natl. Acad. Sci. U.S.A.*, 86, pp. 5227–5231 (1989). Processing by ICE is also necessary for the transport of mature IL-1β through the cell membrane.

ICE, or its homologs, also appears to be involved in the regulation of programmed cell death or apoptosis. Yuan, J. et al., *Cell*, 75, pp. 641–652 (1993); Miura, M. et al., *Cell*, 75, pp. 653–660 (1993); Nett-Fiordalisi, M. A. et al., *J. Cell Biochem.*, 17B, p.117 (1993). In particular, ICE or ICE homologs are thought to be associated with the regulation of apoptosis in neurodegenerative diseases, such as Alzheimer's and Parkinson's disease. Marx, J. and Baringa, M. *Science*, 259, pp. 760–762 (1993); Gagliardini, V. et al., *Science*, 263, pp. 826–828 (1994). Therapeutic applications for inhibition of apoptosis may include treatment of Alzheimer's disease, Parkinson's disease, stroke, myocardial infarction, spinal atrophy, and aging.

ICE has been demonstrated to mediate apoptosis (programmed cell death) in certain tissue types. Steller, H., *Science*, 267, p. 1445 (1995); Whyte, M. and Evan, G., *Nature*, 376, p. 17 (1995); Martin, S. J. and Green, D. R., *Cell*, 82, p. 349 (1995); Alnemri, E. S., et al., *J. Biol. Chem.*, 270, p. 4312 (1995); Yuan, J. *Curr. Opin. Cell Biol.*, 7, p. 211 (1995). A transgenic mouse with a disruption of the ICE gene is deficient in Fas-mediated apoptosis (Kuida, K. et al., *Science* 267, p. 2000 (1995)). This activity of ICE is distinct from its role as the processing enzyme for pro-IL1β. It is conceivable that in certain tissue types, inhibition of ICE may not affect secretion of mature IL-1β, but may inhibit apoptosis.

Enzymatically active ICE has been previously described as a heterodimer composed of two subunits, p20 and p10 (20 kDa and 10 kDa molecular weight, respectively). These subunits are derived from a 45 kDa proenzyme (p45) by way of a p30 form, through an activation mechanism that is autocatalytic. Thornberry, N. A. et al., *Nature*, 356, pp. 768–774 (1992). The ICE proenzyme has been divided into several functional domains: a prodomain (p14), a p22/20 subunit, a polypeptide linker and a p10 subunit. Thornberry et al., supra; Casano et al., *Genomics*, 20, pp. 474–481 (1994).

Full length p45 has been characterized by its cDNA and amino acid sequences. PCT patent applications WO 91/15577 and WO 94/00154. The p20 and p10 cDNA and amino acid sequences are also known. Thornberry et al., supra. Murine and rat ICE have also been sequenced and cloned. They have high amino acid and nucleic acid sequence homology to human ICE. Miller, D. K. et al.,*Ann. N.Y. Acad. Sci.*, 696, pp. 133–148 (1993); Molineaux, S. M. et al., *Proc. Nat. Acad. Sci.*, 90, pp. 1809–1813 (1993). The three-dimensional structure of ICE has been determined at atomic resolution by X-ray crystallography. Wilson, K. P. et al., *Nature*, 370, pp. 270–275 (1994). The active enzyme exists as a tetramer of two p20 and two p10 subunits.

Additionally, there exist human homologs of ICE with sequence similarities in the active site regions of the enzymes. Such homologs include TX (or $ICE_{rel-II}$ or ICH-2) (Faucheu et al., *EMBO J.*, 14, p. 1914 (1995); Kamens J., et al., *J Biol. Chem.*, 270, p. 15250 (1995); Nicholson et al., *J. Biol. Chem.*, 270 p. 15870 (1995)), TY (or $ICE_{rel-III}$) (Nicholson et al., *J. Biol. Chem.*, 270, p. 15870 (1995); ICH-1 (or Nedd-2) (Wang, L. et al., *Cell*, 78, p. 739 (1994)), MCH-2, (Fernandes-Alnemri, T. et al., *Cancer Res.*, 55, p. 2737 (1995), CPP32 (or YAMA or apopain) (Fernandes-Alnemri, T. et al., *J. Biol. Chem.*, 269, p. 30761 (1994); Nicholson, D. W. et al., *Nature*, 376, p. 37 (1995)), and CMH-1 (or MCH-3) (Lippke et al., *J. Biol. Chem.*, (1996); Fernandes-Alnemri, T. et al., *Cancer Res.*, (1995)). Each of these ICE homologs, as well as ICE itself, is capable of inducing apoptosis when overexpressed in transfected cell lines. Inhibition of one or more of these homologs with the peptidyl ICE inhibitor Tyr-Val-Ala-Asp-chloromethylketone results in inhibition of apoptosis in primary cells or cell lines. Lazebnik et al., *Nature*, 371, p. 346 (1994). The compounds described herein are also capable of inhibiting one or more homologs of ICE. Therefore, these compounds may be used to inhibit apoptosis in tissue types that contain ICE homologs.

Interferon-gamma inducing factor (IGIF) is an approximately 18-kDa polypeptide that stimulates T-cell production of interferon-gamma (IFN-γ). IGIF is produced by activated Kupffer cells and macrophages in vivo and is exported out of such cells upon endotoxin stimulation. Thus, a compound that decreases IGIF production would be useful as an inhibitor of such T-cell stimulation which in turn would reduce the levels of IFN-γ production by those cells.

IFN-γ is a cytokine with immunomodulatory effects on a variety of immune cells. In particular, IFN-γ is involved in macrophage activation and Th1 cell selection (Belardelli, F. *APMIS*, 103, p. 161 (1995)). IFN-γ exerts its effects in part by modulating the expression of genes through the STAT and IRF pathways ( Schindler, C., and Darnell, J. E. *Ann. Rev. Biochem.*, 64, p. 621 (1995); Taniguchi, T. *J. Cancer Res. Clin. Oncol.*, 121, p. 516 (1995)).

Mice lacking IFN-γ or its receptor have multiple defects in immune cell function and are resistant to endotoxic shock (Huang, S. et al., *Science*, 259, p. 1742 (1993); Dalton, D. et al., *Science*, 259, p. 1739 (1993); Car, B. D. et al., *J. Exp. Med.*, 179, p. 1437 (1994)). Along with IL-12, IGIF appears to be a potent inducer of IFN-γ production by T cells (Okamura, H. et al., *Infection and Immunity*, 63, p. 3966 (1995); Okamura, H. et al., *Nature*, 378, p. 88 (1995); Ushio, S. et al., *J.Immunol.*, 156, p. 4274 (1996)).

IFN-γ has been shown to contribute to the pathology associated with a variety of inflammatory, infectious and autoimmune disorders and diseases. Thus, compounds capable of decreasing IFN-γ production would be useful to ameliorate the effects of IFN-γ related pathologies.

IGIF is synthesized as a precursor protein, called "pro-IGIF". Recently, ICE and other members of the ICE/CED-3 family have been linked to the conversion of pro-IGIF to IGIF or to IFN-γ production in vivo (PCT application PCT/US96/20843, publication no. WO 97/22619, which is incorporated herein by reference).

Accordingly, compositions and methods capable of regulating the conversion of pro-IGIF to IGIF would be useful for decreasing IGIF and IFN-γ production in vivo, and thus for ameliorating the detrimental effects of these proteins which contribute to human disorders and diseases.

ICE inhibitors represent a class of compounds useful for the control of inflammation or apoptosis or both. Peptide and peptidyl inhibitors of ICE have been described. PCT patent applications WO-91/15577; WO 93/05071; WO93/09135; WO93/14777 and WO- 93/16710; and European patent application 0 547 699. Such peptidyl inhibitors of ICE have been observed to block the production of mature IL-1β in a mouse model of inflammation (vide infra) and to suppress growth of leukemia cells in vitro (Estrov et al., *Blood*, 84, 380a (1994)). However, due to their peptidic nature, such inhibitors are typically characterized by undesirable pharmacological properties, such as poor cellular penetration and cellular activity, poor oral absorption, poor stability and rapid metabolism. Plattner, J. J. and Norbeck, D. W. in *Drug Discovery Technologies, Clark, C. R. and Moos, W. H. Eds. (Ellis Horwood, Chichester, England*, 1990), pp. 92–126. This has hampered their development into effective drugs.

Non-peptidyl compounds have also been reported to inhibit ICE in vitro. PCT patent application WO 95/26958; U.S. Pat. No. 5,552,400; Dolle et al., *J. Med. Chem.*, 39, pp. 2438–2440 (1996). However, it is not clear whether these compounds have the appropriate pharmacological profiles to be therapeutically useful.

Additionally, many methods for the preparation of such compounds are not advantageous. These methods use tributyltin hydride, a toxic, moisture-sensitive reagent. Thus, these methods are inconvenient to carry out, pose a health risk and create toxic-waste disposal problems. Furthermore, it is difficult to purify compounds prepared by these methods. A preferred method for preparing ICE inhibitors has been described in PCT application no. PCT/US/20843, publication no. WO 97/22619 which is incorporated herein by reference.

Accordingly, the need exists for compounds that can effectively inhibit the action of ICE in vivo, for use as agents for preventing and treating chronic and acute forms of IL-1-mediated diseases, apoptosis-, IGIF-, or IFN-γ-mediated diseases, as well as inflammatory, autoimmune, destructive bone, proliferative, infectious, or degenerative diseases.

SUMMARY OF THE INVENTION

The present invention provides novel classes of compounds, and pharmaceutically acceptable derivatives thereof, that are useful as inhibitors of ICE. These compounds can be used alone or in combination with other therapeutic or prophylactic agents, such as antibiotics immunomodulators or other anti-inflammatory agents, for the treatment or prophylaxis of diseases mediated by IL-1, apoptosis, IGIF or IFN-γ. According to a preferred embodiment, the compounds of this invention are capable of binding to the active site of ICE and inhibiting the activity of that enzyme. Additionally, they have improved cellular potency, improved pharmacokinetics, and/or improved oral bioavailability compared to peptidyl ICE inhibitors.

It is a principal object of this invention to provide novel classes of compounds which are inhibitors of ICE represented by formulas:

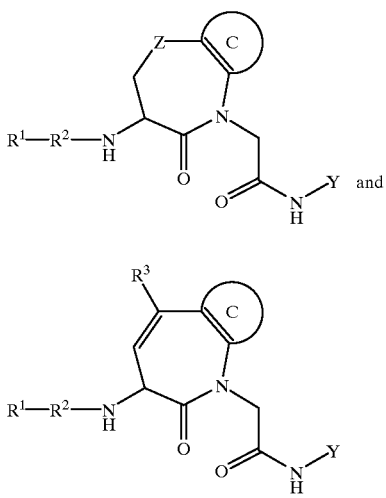

wherein the various substituents are described herein.

It is a further objective of this invention to provide novel processes of preparing the compounds of this invention and related compounds.

DETAILED DESCRIPTION OF THE INVENTION

In order that the invention described herein may be more fully understood, the following detailed description is set forth.

The following abbreviations and definitions are used throughout the application.

| Abbreviations | |
|---|---|
| Ac₂O | acetic anhydride |
| n-Bu | normal-butyl |
| DMF | dimethylformamide |
| DIEA | N,N-diisopropylethylamine |
| EDC | 1-(3-Dimethylaminopropyl)-3-ethylcarbodiimide hydrochloride |
| Et₂O | diethyl ether |
| EtOAc | ethyl acetate |
| Fmoc | 9-fluorenylmethyoxycarbonyl |
| HBTU | O-benzotriazol-1-yl-N,N,N',N'-tetramethyluronium hexafluorophosphate |
| HOBT | 1-hydroxybenzotriazole hydrate |
| MeOH | methanol |
| TFA | trifluoroacetic acid |

The terms "HBV", "HCV" and "HBV" refer to hepatitis-B virus, hepatitis-C virus and hepatitis-G virus, respectively.

The term "$K_i$" refers to a numerical measure of the effectiveness of a compound in inhibiting the activity of a target enzyme such as ICE. Lower values of $K_i$ reflect higher effectiveness. The $K_i$ value is a derived by fitting experimentally determined rate data to standard enzyme kinetic equations (see Segel, I. H. *Enzyme Kinetics*, Wiley-Interscience, 1975).

The term "interferon gamma inducing factor" or "IGIF" refers to a factor which is capable of stimulating the endogenous production of IFN-γ.

The term "ICE inhibitor" refers to a compound which is capable of inhibiting one or more enzymes selected from the group consisting of ICE and ICE homologs. ICE inhibition may be determined using the methods described and incorporated by reference herein. The skilled practitioner realizes that an in vivo ICE inhibitor is not necessarily an in vitro ICE inhibitor. For example, a prodrug form of a compound typically demonstrates little or no activity in in vitro assays. Such prodrug forms may be altered by metabolic or other biochemical processes in the patient to provide an in vivo ICE inhibitor.

The term "cytokine" refers to a molecule which mediates interactions between cells.

The term "condition" refers to any disease, disorder or effect that produces deleterious biological consequences in a subject.

The term "subject" refers to an animal, or to one or more cells derived from an animal. Preferably, the animal is a mammal, most preferably a human. Cells may be in any form, including but not limited to cells retained in tissue, cell clusters, immortalized cells, transfected or transformed cells, and cells derived from an animal that have been physically or phenotypically altered.

The term "patient" as used in this application refers to any mammal, preferably humans.

The term "alkyl" refers to a straight-chained or branched, saturated aliphatic hydrocarbon containing 1 to 6 carbon atoms.

The term "alkenyl" refers to a straight-chained or branched unsaturated hydrocarbon containing 2 to 6 carbons.

The term "cycloalkyl" refers to a mono- or polycyclic, non-aromatic, hydrocarbon ring system which may optionally contain unsaturated bonds in the ring system. Examples include cyclohexyl, adamantyl and norbornyl.

The term "heterocyclic" refers to a mono- or polycyclic ring system which contains 1 to 15 carbon atoms and 1 to 4 heteroatoms, which may optionally contain unsaturated bonds but is not aromatic. Heteroatoms are independently selected from a group including, sulfur, nitrogen and oxygen.

The term "aryl" refers to a mono- or polycyclic ring system which contains 6, 10, 12 or 14 carbons in which at least one ring of the ring system is aromatic. The aryl groups of this invention are optionally singly or multiply substituted with $R^{17}$. Examples of aryl ring systems include, phenyl, naphthyl, and tetrahydronaphthyl.

The term "heteroaryl" refers to a mono- or polycyclic ring system which contains 1 to 15 carbon atoms and 1 to 4 heteroatoms, and in which at least one ring of the ring system is aromatic. Heteroatoms are sulfur, nitrogen or oxygen. The heteroaryl groups of this invention are optionally singly or multiply substituted with $R^{17}$.

The term "heterocyclic" refers to a mono- or polycyclic ring system which contains 1 to 15 carbon atoms and 1 to 4 heteroatoms, in which the mono- or polycyclic ring system may optionally contain unsaturated bonds but is not aromatic. Heteroatoms are independently sulfur, nitrogen, or oxygen.

The term "alkylaryl" refers to an alkyl group, wherein a hydrogen atom of the alkyl group is replaced by an aryl radical.

The term "alkylheteroaryl" refers to an alkyl group, wherein a hydrogen atom of the alkyl group is replaced by a heteroaryl radical.

The term "substitute" refers to the replacement of a hydrogen atom in a compound with a substituent group.

The term "straight chain" refers to a contiguous unbranching string of covalently bound atoms. The straight chain may be substituted, but these substituents are not a part of the straight chain.

In chemical formulas, parenthesis are used herein to denote connectivity in molecules or groups. In particular, parentheses are used to indicate: 1) that more than one atom or group is bonded to a particular atom; or 2) a branching point (i.e., the atom immediately before the open parenthesis is bonded both to the atom or group in the parentheses and the atom or group immediately after the closed parenthesis). An example of the first use is "—N(alkyl)$_2$", indicating two alkyl groups bond to an N atom. An example of the second use is "—C(O)NH$_2$", indicating a carbonyl group and an amino ("NH$_2$") group both bonded to the indicated carbon atom. A "—C(O)NH$_2$" group may be represented in other ways, including the following structure:

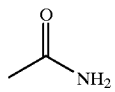

Other definitions are set forth in the specification where necessary.

Compounds of this Invention

The compounds of one embodiment (A) of this invention are those of formula (I):

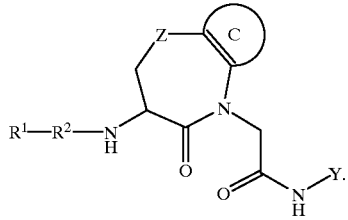

(I)

The compounds of another embodiment (B) of this invention are those of formula (II):

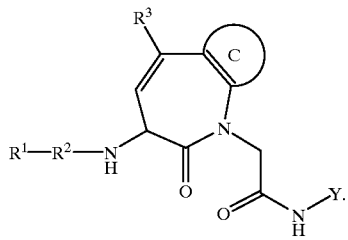

(II)

In embodiments (A) and (B) Y is:

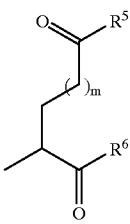

(a)

provided that when $R^5$ is —OH then Y can also be

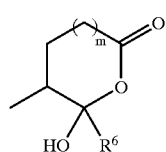

(c)

The compounds of two other embodiments (C) and (D) are those of formulae (I) and (II), respectively, wherein Y is:

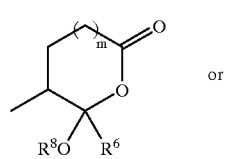

(d)

or

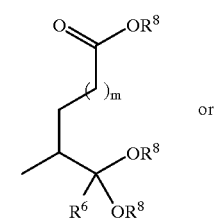

(e)

or

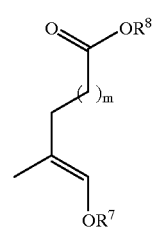

(f)

The substituents in embodiments (A)–(D), are selected from the following groups:

Z is —CH$_2$—, —O—, —S—, —S(O)—, —S(O)$_2$—, —C(O)—, or —C(═N—OR$^{21}$)—;

C is an aryl or heteroaryl ring, wherein the C ring is optionally singly or multiply substituted with —R$^4$;

R$^1$ is -aryl, -heteroaryl, -alkylaryl, or -alkylheteroaryl;

R$^2$ is a bond, —C(O)—, —C(O)C(O)—, —S(O)$_2$—, —OC(O)—, —N(H)C(O)—, —N(H)S(O)$_2$—, —N(H)C(O)C(O)—, —CH═CHCO—, —OCH$_2$C(O)—, —N(H)CH$_2$C(O)—, —N(R$^{19}$)C(O)—, —N(R$^{19}$)S(O)$_2$—, —N(R$^{19}$)C(O)C(O)—, or —N(R$^{19}$)CH$_2$C(O)—;

R$^3$ is —H, -ethynyl, -cyano, -aryl or -heteroaryl, wherein the phenyl and the heteroaryl rings are optionally singly or multiply substituted with —R$^4$;

$R^4$ is —OH, —F, —Cl, —Br, —I, —NO$_2$, —CN, —NH$_2$, —CO$_2$H, —C(O)NH$_2$, —N(H)C(O)H, —N(H)C(O)NH$_2$, -alkyl, -cycloalkyl, -perfluoroalkyl, —O-alkyl, —N(H)alkyl, —N(alkyl)$_2$, —C(O)N(H)alkyl, —C(O)N(alkyl)$_2$, —N(H)C(O)alkyl, —N(H)C(O)N(H)alkyl, —N(H)C(O)N(alkyl)$_2$, —S-alkyl, —S(O)$_2$alkyl, or —C(O)alkyl;

$R^5$ is —OH, —OR$^8$, or —N(H)OH;

$R^6$ is —H, —CH$_2$OR$^9$, —CH$_2$SR$^{10}$, —CH$_2$N(H)R$^9$, —CH$_2$N(R$^9$)R$^{12}$, —C(H)N$_2$, —CH$_2$F, —CH$_2$Cl, —C(O)N(R$^{11}$)R$^{12}$, —R$^{13}$, or —R$^{14}$;

$R^7$ is —C(O)alkyl, —C(O)cycloalkyl, —C(O)alkyenyl, —C(O) alkylaryl, —C(O)alkylheteroaryl, —C(O) heterocycle, or —C(O)alkylheterocycle;

$R^8$ is -alkyl, -cycloalkyl, -aryl, -heteroaryl, -alkylaryl, -alkylheteroaryl, or -alkylheterocycle;

$R^9$ is —H, —C(O)aryl, —C(O)heteroaryl, —C(O) alkylaryl, —C(O) alkylheteroaryl, -alkylaryl, -alkylheteroaryl, or —P(O)R$^{15}$R$^{16}$;

$R^{10}$ is -alkylaryl or -alkylheteroaryl;

$R^{11}$ and $R^{12}$ are independently —H, -alkyl, -aryl, -heteroaryl, -cycloalkyl, -alkylaryl, or -alkylheteroaryl;

$R^{13}$ is -alkylaryl or -alkylheteroaryl;

$R^{14}$ is (i) [structure] or (ii) [structure]

wherein (i) is optionally substituted with one or more —R$^{17}$ and (ii) is optionally substituted with one or more —R$^{17}$, —R$^{18}$ or —R$^{20}$;

$R^{15}$ and $R^{16}$ are independently —H, —OH, -alkyl, -aryl, -heteroaryl, -cycloalkyl, -alkylaryl, -alkylheteroaryl, —Oalkyl, —Oaryl, —Oheteroaryl, —Oalkylaryl, or —Oalkylheteroaryl;

$R^{17}$ is —OH, —F, —Cl, —Br, —I, —NO$_2$, —CN, —NH$_2$, —CO$_2$H, —C(O)NH$_2$, —N(H)C(O)H, —N(H)C(O)NH$_2$, —S(O)$_2$NH$_2$, —C(O)H, -alkyl, -cycloalkyl, -perfluoroalkyl, —O-alkyl, —N(H)alkyl, —N(alkyl)$_2$, —CO$_2$alkyl, —C(O)N(H)alkyl, —C(O)N(alkyl)$_2$, —N(H)C(O)alkyl, —N(H)C(O)N(H)alkyl, —N(H)C(O)N(alkyl)$_2$, —S(O)$_2$N(H)alkyl, —S(O)$_2$N(alkyl)$_2$, —S—alkyl, —S(O)$_2$alkyl, or —C(O)alkyl;

$R^{18}$ is -aryl, -heteroaryl, -alkylaryl, -alkylheteroaryl, —O-aryl, —O-heteroaryl, —O-alkylaryl, —O-alkylheteroaryl, —N(H)aryl, —N(aryl)$_2$, —N(H)heteroaryl, —N(heteroaryl)$_2$, —N(H)alkylaryl, —N(alkylaryl)$_2$, —N(H)alkylheteroaryl, —N(alkylheteroaryl)$_2$, —S-aryl, —S—heteroaryl, —S-alkylaryl, —S-alkylheteroaryl, —C(O)aryl, —C(O)heteroaryl, —C(O)alkylaryl, —C(O)alkylheteroaryl, —CO$_2$aryl, —CO$_2$heteroaryl, —CO$_2$alkylaryl, —CO$_2$alkylheteroaryl, —C(O)N(H)aryl, —C(O)N(aryl)$_2$, —C(O)N(H)heteroaryl, —C(O)N(heteroaryl)$_2$, —C(O)N(H)alkylaryl, —C(O)N(alkylaryl)$_2$, —C(O) N(H)alkylheteroaryl, —C(O) N(alkylheteroaryl)$_2$, —S(O)$_2$-aryl, —S(O)$_2$-heteroaryl, —S(O)$_2$-alkylaryl, —S(O)$_2$-alkylheteroaryl, —S(O)$_2$N(H)-aryl, —S(O)$_2$N(H)-heteroaryl, —S(O)$_2$N(H)-alkylaryl, —S(O)$_2$N(H)-alkylheteroaryl, —S(O)$_2$N(aryl)$_2$, —S(O)$_2$N(heteroaryl)$_2$, —S(O)$_2$N(alkylaryl)$_2$, —S(O)$_2$N(alkylheteroaryl)$_2$, —N(H)C(O)N(H)aryl, —N(H)C(O)N(H)heteroaryl, —N(H)C(O)N(H)alkylaryl, —N(H)C(O)N(H)alkylheteroaryl, —N(H)C(O)N(aryl)$_2$, —N(H)C(O)N(heteroaryl)$_2$, —N(H)C(O)N(alkylaryl)$_2$, or —N(H)C(O)N(alkylheteroaryl)$_2$;

$R^{19}$ is —H, -alkyl, -cycloalkyl, -aryl, -heteroaryl, -alkylaryl, or -alkylheteroaryl, or -alkylheterocycle;

$R^{20}$ is -alkyl-R$^{18}$;

$R^{21}$ is H, alkyl, alkylaryl, or alkylheteroaryl;

m is 0 or 1; and

X is O or S.

Preferably, Z is —O— and the other substituents are as defined above.

Alternatively, Z is —S— and the other substituents are as defined above.

Alternatively, Z is —C(O)— and the other substituents are as defined above.

Preferably, in these preferred compounds, C is benzo, pyrido, thieno, pyrrolo, furo, imidazo, thiazolo, oxazolo, pyrazolo, isothiazolo, isoxazolo, and triazolo, wherein the C ring is optionally singly or multiply substituted with —R$^4$ and the other substituents are as defined above.

More preferably:

C is benzo;

Z is —O—, —S—, or —C(O)—;

Y is:

[structures]

$R^1$ is phenyl, naphthyl, or isoquinolinyl wherein R$^{17}$ is —OH, —NH$_2$, —Cl, —F, —Oalkyl, or —N(alkyl)$_2$;

$R^2$ is —C(O)—, —S(O)$_2$—, —C(O)C(O)— or —CH$_2$C(O)—;

$R^4$ is fluoro or chloro;

$R^5$ is —OH;

$R^6$ is —H or —R$^{14}$ wherein X is O and for formula (i) R$^{17}$ is —Oalkyl, —F or —Cl and for formula (ii) R$^{18}$ is aryl wherein aryl is phenyl;

$R^7$ is —C(O)alkyl;

$R^8$ is methyl, ethyl, n-propyl, isopropyl, cyclopentyl, phenethyl, or benzyl;

X is O; or m is 0.

More preferably, in these more preferred compounds, Y is (a) or R$^6$ is H.

Most preferably, $R^1$ is isoquinolyl or Z is —C(O)—.

Preferred compounds of this invention include, but are not limited to:

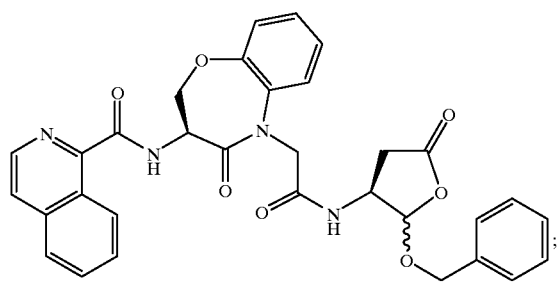
5a
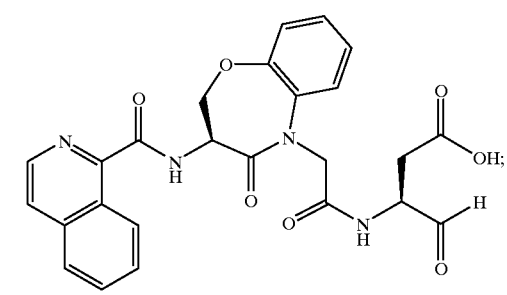
6a
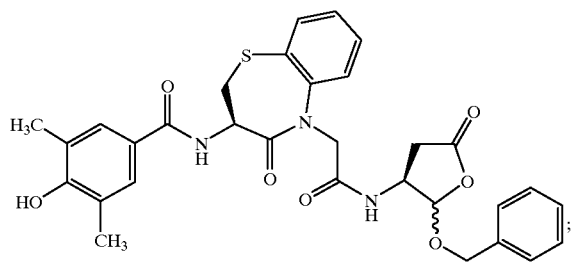
10a
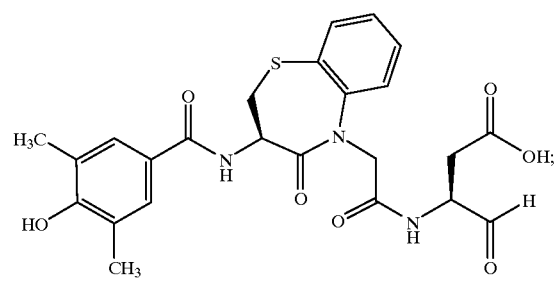
11a
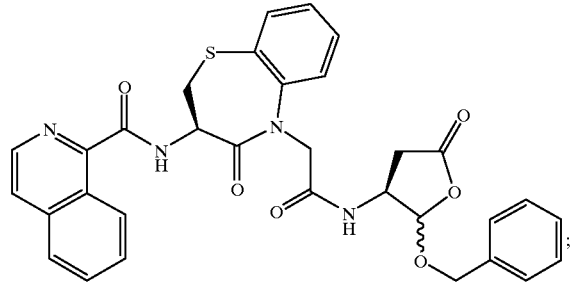
10b
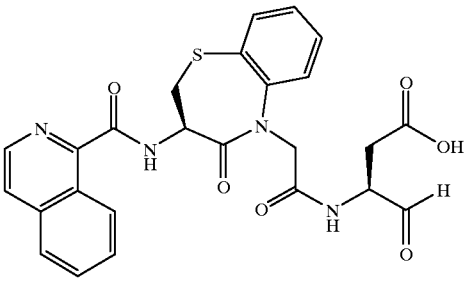
11b
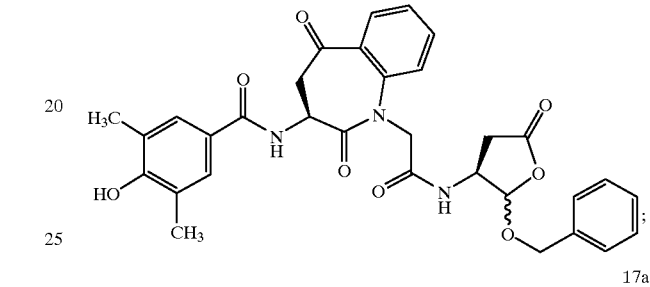
16a
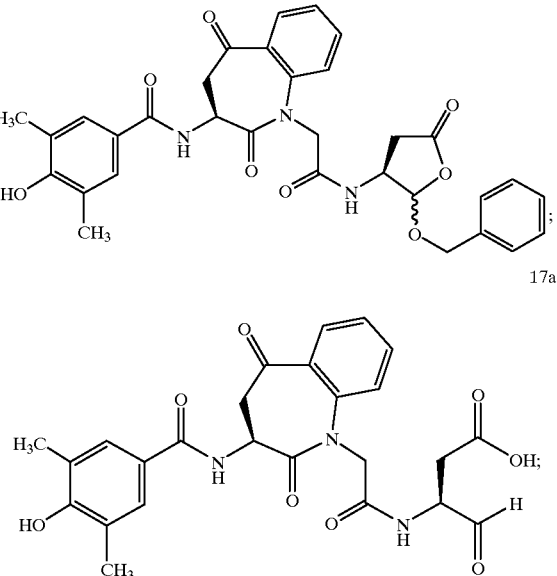
17a
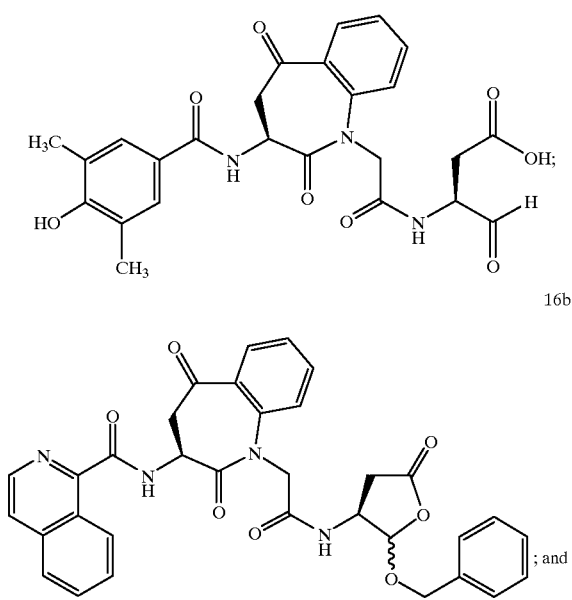
16b
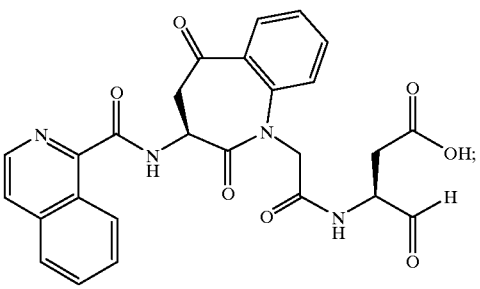
17b
; and
We now prefer compounds of embodiments (E)–(H). The compounds of embodiment (E) of this invention are those of formula (III):

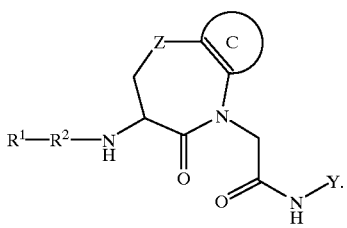

(III)

The compounds of embodiment (F) of this invention are those of formula (IV):

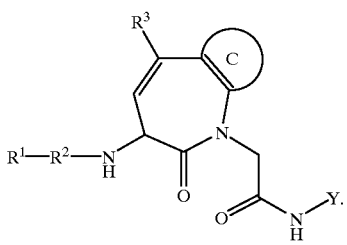

(IV)

In embodiments (E) and (F) Y is:

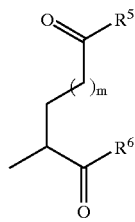

(a)

provided that when $R^5$ is —OH then Y can also be

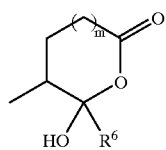

(c)

The compounds of other embodiments (G) and (H) are those of formulae (III) and (IV), respectively, wherein Y is:

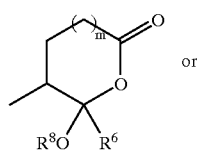

(d)

or

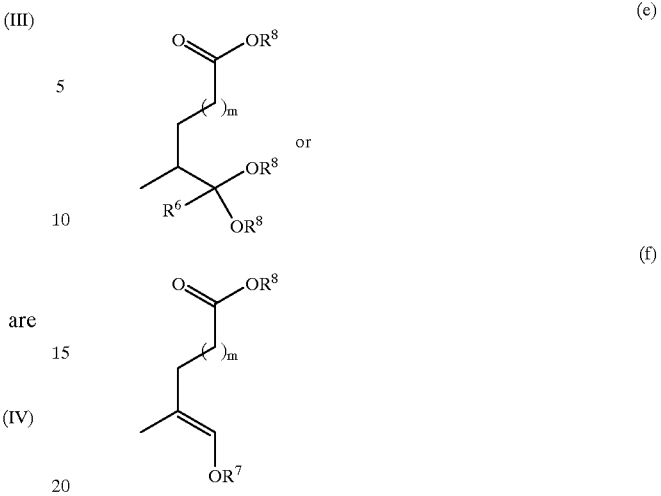

(e)

or (f)

The substituents in embodiments (E)–(H), are selected from the following groups:

Z is —CH$_2$—, —O—, —S—, —S(O)—, —S(O)$_2$—, —C(O)—, or —C(=N—OR$^{21}$)—;

C is an aryl or heteroaryl ring, wherein the C ring is optionally singly or multiply substituted with —R$^4$;

R$^1$ is -aryl, -heteroaryl, -alkylaryl, or -alkylheteroaryl;

R$^2$ is a bond, —C(O)—, —C(O)C(O)—, —S(O)$_2$—, —OC(O)—, —N(H)C(O)—, —N(H)S(O)$_2$—, —N(H)C(O)C(O)—, —CH=CHCO—, —OCH$_2$C(O)—, —N(H)CH$_2$C(O)—, —N(R$^{19}$)C(O)—, —N(R$^{19}$)S(O)$_2$—, —N(R$^{19}$)C(O)C(O)—, or —N(R$^{19}$)CH$_2$C(O)—;

R$^3$ is H, ethynyl, cyano, aryl or heteroaryl, wherein the phenyl and the heteroaryl rings are optionally singly or multiply substituted with —R$^4$;

R$^4$ is —OH, —F, —Cl, —Br, —I, —NO$_2$, —CN, —NH$_2$, —CO$_2$H, —C(O)NH$_2$, —N(H)C(O)H, —N(H)C(O)NH$_2$, -alkyl, -cycloalkyl, -perfluoroalkyl, —O-alkyl, —N(H)alkyl, —N(alkyl)$_2$, —C(O)N(H)alkyl, —C(O)N(alkyl)$_2$, —N(H)C(O)alkyl, —N(H)C(O)N(H)alkyl, —N(H)C(O)N(alkyl)$_2$, —S-alkyl, —S(O)$_2$alkyl, —C(O)alkyl, —CH$_2$NH$_2$, —CH$_2$N(H)alkyl, or —CH$_2$N(alkyl)$_2$;

R$^5$ is —OH, —OR$^8$, or —N(H)OH;

R$^6$ is —H, —CH$_2$OR$^9$, —CH$_2$SR$^{10}$, —CH$_2$N(H)R$^9$, —CH$_2$N(R$^9$)R$^{12}$, —C(H)N$_2$, —CH$_2$F, —CH$_2$Cl, —C(O)N(R$^{11}$)R$^{12}$, —R$^{13}$, or —R$^{14}$;

R$^7$ is —C(O)alkyl, —C(O)cycloalkyl, —C(O)alkyenyl, —C(O) alkylaryl, —C(O)alkylheteroaryl, —C(O) heterocycle, or —C(O)alkylheterocycle;

R$^8$ is -alkyl, -cycloalkyl, -aryl, -heteroaryl, -alkylaryl, -alkylheteroaryl, or -alkylheterocycle;

R$^9$ is —H, —C(O)aryl, —C(O)heteroaryl, —C(O) alkylaryl, —C(O)alkylheteroaryl, -alkylaryl, -alkylheteroaryl, -aryl, -heteroaryl, or —P(O)R$^{15}$R$^{16}$;

R$^{10}$ is -alkylaryl or -alkylheteroaryl;

R$^{11}$ and R$^{12}$ are independently —H, -alkyl, -aryl, -heteroaryl, -cycloalkyl, -alkylaryl, or -alkylheteroaryl;

R$^{13}$ is -alkylaryl or -alkylheteroaryl;

$R^{14}$ is (i)

[structure: benzo-fused 5-membered ring with X and N, methyl substituent] or (ii)

[structure: 5-membered ring with X and N, methyl substituent]

wherein (i) is optionally substituted with one or more —$R^{17}$ and (ii) is optionally substituted with one or more —$R^{17}$, —$R^{18}$ or —$R^{20}$;

$R^{15}$ and $R^{16}$ are independently —H, —OH, -alkyl, -aryl, -heteroaryl, -cycloalkyl, -alkylaryl, -alkylheteroaryl, —Oalkyl, —Oaryl, —Oheteroaryl, —Oalkylaryl, or —Oalkylheteroaryl;

$R^{17}$ is —OH, —F, —Cl, —Br, —I, —NO$_2$, —CN, —NH$_2$, —CO$_2$H, —C(O)NH$_2$, —N(H)C(O)H, —N(H)C(O)NH$_2$, —SO$_2$NH$_2$, —C(O)H, -alkyl, -cycloalkyl, -perfluoroalkyl, —O-alkyl, —N(H)alkyl, —N(alkyl)$_2$, —CO$_2$alkyl, —C(O)N(H)alkyl, —C(O)N(alkyl)$_2$, —N(H)C(O)alkyl, —N(H)C(O)N(H)alkyl, —N(H)C(O)N(alkyl)$_2$, —S(O)$_2$N(H)alkyl, —S(O)$_2$N(alkyl)$_2$, —S—alkyl, —S(O)$_2$alkyl, or —C(O)alkyl;

$R^{18}$ is -aryl, -heteroaryl, -alkylaryl, -alkylheteroaryl, —O-aryl, —O-heteroaryl, —O-alkylaryl, —O-alkylheteroaryl, —N(H)aryl, —N(aryl)$_2$, —N(H)heteroaryl, —N(heteroaryl)$_2$, —N(H)alkylaryl, —N(alkylaryl)$_2$, —N(H)alkylheteroaryl, —N(alkylheteroaryl)$_2$, —S-aryl, —S-heteroaryl, —S—alkylaryl, —S-alkylheteroaryl, —C(O)aryl, —C(O)heteroaryl, —C(O) alkylaryl, —C(O) alkylheteroaryl, —CO$_2$aryl, —CO$_2$heteroaryl, —CO$_2$alkylaryl, —CO$_2$alkylheteroaryl, —C(O)N(H)aryl, —C(O)N(aryl)$_2$, —C(O)N(H)heteroaryl, —C(O)N(heteroaryl)$_2$, —C(O)N(H)alkylaryl), —C(O)N(alkylaryl)$_2$, —C(O)N(H)alkylheteroaryl, —C(O)N(alkylheteroaryl)$_2$, —S(O)$_2$-aryl, —S(O)$_2$-heteroaryl, —S(O)$_2$-alkylaryl, —S(O)$_2$-alkylheteroaryl, —S(O)$_2$N(H)-aryl, —S(O)$_2$NH-heteroaryl, —S(O)$_2$N(H)-alkylaryl, —S(O)$_2$N(H)-alkylheteroaryl, —S(O)$_2$N(aryl)$_2$, —S(O)$_2$N(heteroaryl)$_2$, —S(O)$_2$N(alkylaryl)$_2$, —S(O)$_2$N(alkylheteroaryl)$_2$, —N(H)C(O)N(H)aryl, —N(H)C(O)N(H)heteroaryl, —N(H)C(O)N(H)alkylaryl, —N(H)C(O)N(H)alkylheteroaryl, —N(H)C(O)N(aryl)$_2$, —N(H)C(O)N(heteroaryl)$_2$, —N(H)C(O)N(alkylaryl)$_2$, or —N(H)C(O)N(alkylheteroaryl)$_2$;

$R^{19}$ is —H, -alkyl, -cycloalkyl, -aryl, -heteroaryl, -alkylaryl, or -alkylheteroaryl, or -alkylheterocycle;

$R^{20}$ is -alkyl-$R^{18}$;

$R^{21}$ is H, alkyl, alkylaryl, or alkylheteroaryl;

m is 0 or 1; and

X is O or S;

provided that in embodiment (E), when
$R^1$ is aryl, wherein aryl is phenyl;
$R^2$ is —OC(O)—;
C is aryl, wherein aryl is phenyl
m is 0; and
$R^5$ is OH, then
$R^6$ cannot be —CH$_2$OR$_9$, wherein $R^9$ is:
—C(O)aryl, and aryl is 2,6-dichlorophenyl, or
1-(4-chlorophenyl)-3-trifluoromethylpyrazole-5-yl.

In the above embodiments, $R^8$ and $R^{19}$ may also independently be heterocyclyl or alkylcycloalkyl.

Preferably, Z is —O— and the other substituents are as defined above.

More preferably in embodiment (E), when $R^6$ is —CH$_2$OR$_9$ and $R^9$ is —C(O)aryl, aryl is not 2,6-dichlorophenyl; and when $R^9$ is -heteroaryl, heteroaryl is not pyrazol-5-yl.

Most preferably in embodiment (E), when $R^6$ is —CH$_2$OR$_9$ and $R^9$ is -heteroaryl, heteroaryl is not pyrazolyl; and when $R^9$ is —P(O)$R^{15}R^{16}$, wherein $R^{15}$ and $R^{16}$ are aryl, aryl is not phenyl;

Alternatively, Z is —S—.

Alternatively, Z is —C(O)—.

Preferably,

C is benzo, pyrido, thieno, pyrrolo, furo, imidazo, thiazolo, oxazolo, pyrazolo, isothiazolo, isoxazolo, and triazolo, wherein the C ring is optionally singly or multiply substituted with —$R^4$;

Y is:

(a)

[structure: chain with C=O–$R^5$, (CH$_2$)$_m$, methyl, C(=O)–$R^6$] or (c)

[structure: 6-membered lactone ring with HO and $R^6$ substituents, (CH$_2$)$_m$]

$R^1$ is phenyl, naphthyl, or isoquinolinyl wherein $R^{17}$ is —OH, —NH$_2$, —Cl, —F, —Oalkyl, or —N(alkyl)$_2$;

$R^2$ is —C(O)—, —S(O)$_2$—, —C(O)C(O)— or —CH$_2$C(O)—;

$R^4$ is fluoro or chloro;

$R^5$ is —OH;

$R^6$ is —H or —$R^{14}$ wherein x is O and for formula (i) $R^{17}$ is —Oalkyl, —F or —Cl and for formula (ii) $R^{18}$ is aryl wherein aryl is phenyl;

$R^7$ is —C(O)alkyl;

$R^8$ is methyl, ethyl, n-propyl, isopropyl, cyclopentyl, phenethyl, or benzyl;

$R^9$ is —C(O)aryl, —C(O)heteroaryl, —C(O)alkylaryl, —C(O) alkylheteroaryl, -alkylaryl, -alkylheteroaryl, -aryl, or -heteroaryl;

X is O; or m is 0.

More preferably, C is benzo, Y is (a), and $R^6$ is H.

In other preferred and more preferred compounds Y is (d), $R^6$ is H, and the other substituents are as described above.

Most preferably, $R^1$ is isoquinolyl or Z is —C(O)—.

Other preferred compounds of this invention include, but are not limited to:

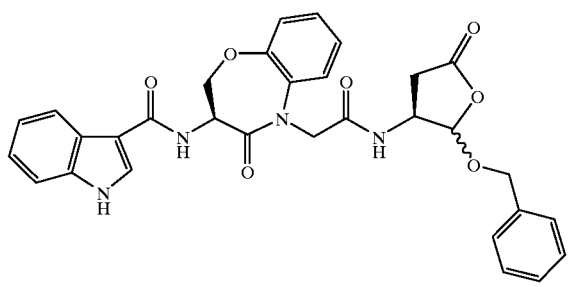

5c

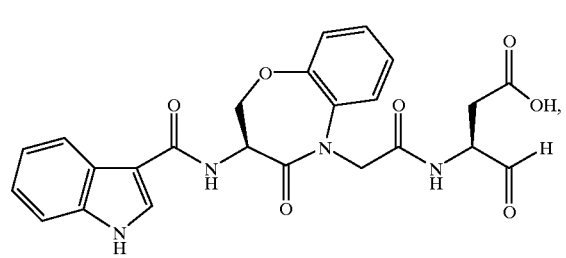

6c

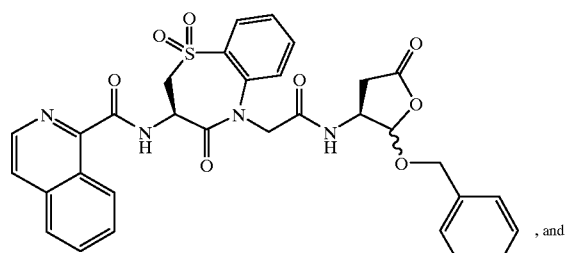

, and

18a

19a

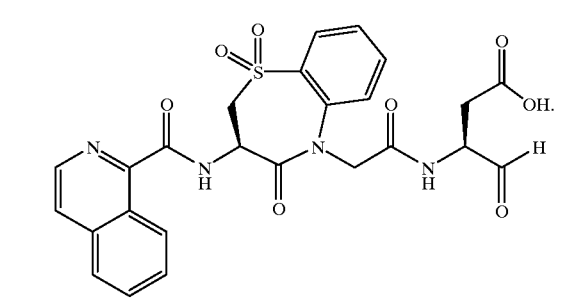

The ICE inhibitors of this invention may contain one or more "asymmetric" carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration. Although specific compounds and scaffolds exemplified in this application may be depicted in a particular stereochemical configuration, compounds and scaffolds having either the opposite stereochemistry at any given chiral center or mixtures thereof are also envisioned.

When multiply substituted, each substituent may be picked independently of any other substituent as long as the combination of substituents results in the formation of a stable compound.

Combinations of substituents and variables envisioned by this invention are only those that result in the formation of stable compounds. The term "stable", as used herein, refers to compounds which possess stability sufficient to allow manufacture and administration to a mammal by methods known in the art. Typically, such compounds are stable at a temperature of 40 ° C. or less, in the absence of moisture or other chemically reactive conditions, for at least a week.

Substituents may be represented in various forms. These various forms are known to the skilled practitioner and may be used interchangeably. For example, a methyl substituent on a phenyl ring may be represented in any of the following forms:

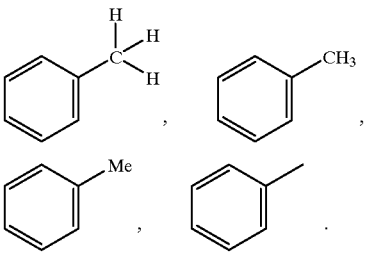

Various forms of substituents such as methyl are used herein interchangeably.

The compounds of this invention have a molecular weight of less than or equal to about 700 Daltons, and more preferably between about 400 and 600 Daltons. These preferred compounds may be readily absorbed by the bloodstream of patients upon oral administration. This oral availability makes such compounds excellent agents for orally-administered treatment and prevention regimens against IL-1-, apoptosis-, IGIF-, or IFN-γ-mediated diseases.

It should be understood that the compounds of this invention may exist in various equilibrium forms, depending on conditions including choice of solvent, pH, and others known to the practitioner skilled in the art. All such forms of these compounds are expressly included in the present invention. In particular, many of the compounds of this invention, especially those which contain aldehyde or ketone groups in $R_3$ and carboxylic acid groups in T, may take hemiketal (or hemi-acetal) or hydrated forms. For example, compounds of embodiment (A) take a hemiacetal or hemiketal form when Y is:

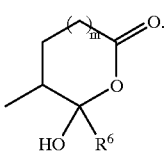

Depending on the choice of solvent and other conditions known to the practitioner skilled in the art, compounds of this invention may also take hydrated, acyloxy ketal, acyloxy acetal, ketal, acetal or enol forms. For example, in embodiment B compounds of this invention take hydrated forms when Y is:

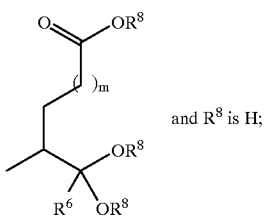

and R[8] is H;

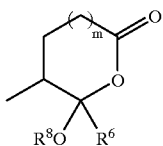

acyloxy ketal or acyloxy acetal forms when Y is:

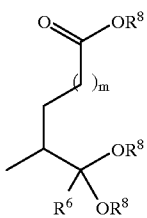

ketal or acetal forms when Y is:

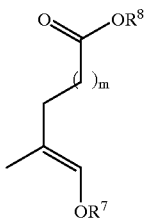

and enol forms when Y is:

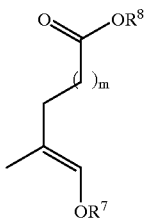

In addition, it should be understood that the equilibrium forms of the compounds of this invention may include tautomeric forms. All such forms of these compounds are expressly included in the present invention.

It should be understood that the compounds of this invention may be modified by appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion. In addition, the compounds may be altered to pro-drug form such that the desired compound is created in the body of the patient as the result of the action of metabolic or other biochemical processes on the pro-drug. Such pro-drug forms typically demonstrate little or no activity in in vitro assays. Some examples of pro-drug forms include ketal, acetal, oxime, imine and hydrazone forms of compounds which contain ketone or aldehyde groups, especially where they occur in the $R^3$ group of the compounds of this invention. Other examples of pro-drug forms include the hemiketal, hemiacetal, acyloxy ketal, acyloxy acetal, ketal, acetal and enol forms that are described herein.

Compositions and Methods

The compounds of this invention are excellent ligands for ICE. Accordingly, these compounds are capable of targeting and inhibiting events in IL-1-, apoptosis-, IGIF- and IFN-γ-mediated diseases, and, thus, the ultimate activity of that protein in inflammatory diseases, autoimmune diseases, destructive bone, proliferative disorders, infectious diseases, and degenerative diseases. For example, the compounds of this invention inhibit the conversion of precursor IL-1β to mature IL-1β by inhibiting ICE. Because ICE is essential for the production of mature IL-1, inhibition of that enzyme effectively blocks initiation of IL-1-mediated physiological effects and symptoms, such as inflammation, by inhibiting the production of mature IL-1. Thus, by inhibiting IL-1β precursor activity, the compounds of this invention effectively function as IL-1 inhibitors.

Compounds of this invention also inhibit conversion of pro-IGIF into active, mature IGIF by inhibiting ICE. Because ICE is essential for the production of mature IGIF, inhibition of ICE effectively blocks initiation of IGIF-mediated physiological effects and symptoms, by inhibiting production of mature IGIF. IGIF is in turn essential for the production of IFN-γ. ICE therefore effectively blocks initiation of IFN-γ-mediated physiological effects and symptoms, by inhibiting production of mature IGIF and thus production of IFN-γ.

The pharmaceutical compositions and methods of this invention, therefore, will be useful for controlling ICE activity in vivo. The compositions and methods of this invention will thus be useful for controlling IL-1, IGIF or IFN-γ levels in vivo and for treating or reducing the advancement, severity or effects of IL-1-, apoptosis-, IGIF-, or IFN-γ-mediated conditions, including diseases, disorders or effects.

Accordingly, one embodiment of this invention provides a method for decreasing IGIF production in a subject comprising the step of administering to the subject a pharmaceutical composition comprising a therapeutically effective amount of an ICE inhibitor and a pharmaceutically acceptable carrier.

Another embodiment of this invention provides a method for decreasing IFN-γ production in a subject comprising the step of administering to the subject a pharmaceutical composition comprising a therapeutically effective amount of an ICE inhibitor and a pharmaceutically acceptable carrier.

In another embodiment, the methods of this invention comprise the step of administering to a subject a pharmaceutical composition comprising an inhibitor of an ICE-related protease that is capable of cleaving pro-IGIF to active IGIF, and a pharmaceutically acceptable carrier. One such ICE-related protease is TX, as described above. This invention thus provides methods and pharmaceutical compositions for controlling IGIF and IFN-γ levels by administering a TX inhibitor.

Other ICE-related proteases capable of processing pro-IGIF into an active IGIF form may also be found. Thus it is envisioned that inhibitors of those enzymes may be identified by those of skill in the art and will also fall within the scope of this invention.

Pharmaceutical compositions of this invention comprise an ICE inhibitor or a pharmaceutically acceptable salt thereof and a pharmaceutically acceptable carrier, adjuvant or vehicle. Such compositions may optionally comprise an additional therapeutic agent. Such agents include, but are not limited to, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

If the pharmaceutical composition comprises only the ICE inhibitor as the active component, such methods may additionally comprise the step of administering to the subject an additional agent. Such agents include, but are not limited to, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The term "pharmaceutically effective amount" refers to an amount effective in treating or ameliorating an IL-1-, apoptosis-, IGIF- or IFN-γ-mediated disease in a patient. The term "prophylactically effective amount" refers to an amount effective in preventing or substantially lessening IL-1-, apoptosis-, IGIF- or IFN-γ-mediated diseases in a patient.

The term "pharmaceutically acceptable carrier or adjuvant" refers to a non-toxic carrier or adjuvant that may be administered to a patient, together with a compound of this invention, and which does not destroy the pharmacological activity thereof.

The term "pharmaceutically acceptable derivative" means any pharmaceutically acceptable salt, ester, or salt of such ester, of a compound of this invention or any other compound which, upon administration to a recipient, is capable of providing (directly or indirectly) a compound of this invention or an anti-ICE active metabolite or residue thereof.

Pharmaceutically acceptable salts of the compounds of this invention include, for example, those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N—$(C_{1-4}$ alkyl$)_4^+$ salts.

This invention also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

The compounds of this invention may be employed in a conventional manner for controlling IGIF and IFN-γ levels in vivo and for treating diseases or reducing the advancement or severity of effects which are mediated by IL-1, apoptosis, IGIF or IFN-γ. Such methods of treatment, their dosage levels and requirements may be selected by those of ordinary skill in the art from available methods and techniques.

For example, a compound of this invention may be combined with a pharmaceutically acceptable adjuvant for administration to a patient suffering from an IL-1-, apoptosis-, IGIF- or IFN-γ-mediated disease in a pharmaceutically acceptable manner and in an amount effective to lessen the severity of that disease.

Alternatively, the compounds of this invention may be used in compositions and methods for treating or protecting individuals against IL-1, apoptosis-, IGIF, or IFN-γ mediated diseases over extended periods of time. The compounds may be employed in such compositions either alone or together with other compounds of this invention in a manner consistent with the conventional utilization of ICE inhibitors in pharmaceutical compositions. For example, a compound of this invention may be combined with pharmaceutically acceptable adjuvants conventionally employed in vaccines and administered in prophylactically effective amounts to protect individuals over an extended period of time against IL-1-, apoptosis-, IGIF, or IFN-γ mediated diseases.

The compounds of this invention may also be co-administered with other ICE inhibitors to increase the effect of therapy or prophylaxis against various IL-1-, apoptosis-, IGIF- or IFN-γ mediated diseases.

In addition, the compounds of this invention may be used in combination either conventional anti-inflammatory agents or with matrix metalloprotease inhibitors, lipoxygenase inhibitors and antagonists of cytokines other than IL-1β.

The compounds of this invention can also be administered in combination with immunomodulators (e.g., bropirimine, anti-human alpha-interferon antibody, IL-2, GM-CSF, methionine enkephalin, interferon-alpha, diethyldithiocarbamate, tumor necrosis factor, naltrexone and EPO), with prostaglandins, or with antiviral agents (e.g., 3TC, polysulfated polysaccharides, ganiclovir, ribavirin, acyclovir, alpha interferon, trimethotrexate and fancyclovir) or prodrugs of these or related compounds to prevent or combat IL-1-mediated disease symptoms such as inflammation.

When the compounds of this invention are administered in combination therapies with other agents, they may be administered sequentially or concurrently to the patient. Alternatively, pharmaceutical or prophylactic compositions according to this invention comprise a combination of an ICE inhibitor of this invention and another therapeutic or prophylactic agent.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, wool fat and self-emulsifying drug delivery systems (SEDDS) such as α-tocopherol, polyethyleneglycol 1000 succinate, or other similar polymeric delivery matrices.

The pharmaceutical compositions of this invention may be administered orally, parenterally, by inhalation spray, topically, rectally, nasally, buccally, vaginally or via an implanted reservoir. We prefer oral administration. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as those described in Pharmacopeia Helvetica, *Ph. Helv*, or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-administered transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of IL-1-, apoptosis-, IGIF- and IFN-$\gamma$ mediated diseases, including inflammatory diseases, autoimmune diseases, destructive bone disorders, proliferative disorders, infectious diseases, degenerative diseases, necrotic diseases, osteoarthritis, acute pancreatitis, chronic pancreatitis, asthma, adult respiratory distress syndrome, glomerulonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, chronic active hepatitis, myasthenia gravis, inflammatory bowel disease, Crohn's disease, psoriasis, graft vs. host disease, osteoporosis, multiple myeloma-related bone disorder, acute myelogenous leukemia, chronic myelogenous leukemia, metastatic melanoma, Kaposi's sarcoma, multiple myeloma, sepsis, septic shock, Shigellosis, Alzheimer's disease, Parkinson's disease, cerebral ischemia, myocardial ischemia, spinal muscular atrophy, multiple sclerosis, AIDS-related encephalitis, HIV-related encephalitis, aging, alopecia, neurological damage due to stroke, ulcerative collitis, infectious hepatitis, juvenile diabetes, lichenplanus, acute dermatomyositis, eczema, primary cirrhosis, uveitis, Behcet's disease, atopic skin disease, pure red cell aplasia, aplastic anemia, amyotrophic lateral sclerosis, nephrotic syndrome and systemic diseases or diseases with effects localized in the liver or other organs having an inflammatory or apoptotic component caused by excess dietary alcohol intake or viruses, such as HBV, HCV, HGV, yellow fever virus, dengue fever virus, and Japanese encephalitis virus.

Typically, the pharmaceutical compositions of this invention will be administered from about 1 to 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of an ICE inhibitor and one or more additional therapeutic or prophylactic agents, both the ICE inhibitor and the additional agent should be present at dosage levels of between about 10% to 80% of the dosage normally administered in a monotherapy regime.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence or disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

The IL-1 mediated diseases which may be treated or prevented by the compounds of this invention include, but are not limited to, inflammatory diseases, autoimmune diseases, proliferative disorders, infectious diseases, and degenerative diseases. The apoptosis-mediated diseases which may be treated or prevented by the compounds of this invention include degenerative diseases.

IL-1 mediated inflammatory diseases which may be treated or prevented include, but are not limited to osteoarthritis, acute pancreatitis, chronic pancreatitis, asthma, and adult respiratory distress syndrome. Preferably the inflammatory disease is osteoarthritis or acute pancreatitis.

IL-1 mediated autoimmune diseases which may be treated or prevented include, but are not limited to, glomerulonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, chronic active hepatitis, myasthenia gravis, multiple sclerosis, inflammatory bowel disease, Crohn's disease, psoriasis, and graft vs. host disease. Preferably the autoimmune disease is rheumatoid arthritis, inflammatory bowel disease, Crohn's disease, or psoriasis, IL-1 mediated destructive bone disorders which may be treated or prevented include, but are not limited to, osteoporosis and multiple myeloma-related bone disorder.

IL-1 mediated proliferative diseases which may be treated or prevented include, but are not limited to, acute myelogenous leukemia, chronic myelogenous leukemia, metastatic melanoma, Kaposi's sarcoma, and multiple myeloma.

IL-1 mediated infectious diseases which may be treated or prevented include, but are not limited to, sepsis, septic shock, and Shigellosis.

The IL-1-mediated degenerative or necrotic diseases which may be treated or prevented by the compounds of this invention include, but are not limited to, Alzheimer's disease, Parkinson's disease, cerebral ischemia, and myocardial ischemia. Preferably, the degenerative disease is Alzheimer's disease.

The apoptosis-mediated degenerative diseases which may be treated or prevented by the compounds of this invention include, but are not limited to, Alzheimer's disease, Parkinson's disease, cerebral ischemia, myocardial ischemia, spinal muscular atrophy, multiple sclerosis, AIDS-related encephalitis, HIV-related encephalitis, aging, alopecia, and neurological damage due to stroke.

Other diseases having an inflammatory or apoptotic component may be treated or prevented by the compounds of this invention. Such diseases may be systemic diseases or diseases with effects localized in the liver or other organs and may be caused by, for example, excess dietary alcohol intake or viruses, such as HBV, HCV, HGV, yellow fever virus, dengue fever virus, and Japanese encephalitis virus.

The IGIF- or IFN-γ-mediated diseases which may be treated or prevented by the compounds of this invention include, but are not limited to, inflammatory, infectious, autoimmune, proliferative, neurodegenerative and necrotic conditions.

IGIF- or IFN-γ-mediated inflammatory diseases which may be treated or prevented include, but are not limited to osteoarthritis, acute pancreatitis, chronic pancreatitis, asthma, rheumatoid arthritis, inflammatory bowel disease, Crohn's disease, ulcerative collitis, cerebral ischemia, myocardial ischemia and adult respiratory distress syndrome. Preferably, the inflammatory disease is rheumatoid arthritis, ulcerative collitis, Crohn's disease, hepatitis or adult respiratory distress syndrome.

IGIF- or IFN-γ-mediated infectious diseases which may be treated or prevented include, but are not limited to infectious hepatitis, sepsis, septic shock and Shigellosis.

IGIF- or IFN-γ-mediated autoimmune diseases which may be treated or prevented include, but are not limited to glomerulonephritis, systemic lupus erythematosus, scleroderma, chronic thyroiditis, Graves' disease, autoimmune gastritis, insulin-dependent diabetes mellitus (Type I), juvenile diabetes, autoimmune hemolytic anemia, autoimmune neutropenia, thrombocytopenia, myasthenia gravis, multiple sclerosis, psoriasis, lichenplanus, graft vs. host disease, acute dermatomyositis, eczema, primary cirrhosis, hepatitis, uveitis, Behcet's disease, atopic skin disease, pure red cell aplasia, aplastic anemia, amyotrophic lateral sclerosis and nephrotic syndrome. Preferably, the autoimmune disease is glomerulonephritis, insulin-dependent diabetes mellitus (Type I), juvenile diabetes, psoriasis, graft vs. host disease or hepatitis.

Although this invention focuses on the use of the compounds disclosed herein for preventing and treating IL-1, apoptosis-, IGIF, IFN-γ-mediated diseases, the compounds of this invention can also be used as inhibitory agents for other cysteine proteases.

The compounds of this invention are also useful as commercial reagents which effectively bind to ICE or other cysteine proteases. As commercial reagents, the compounds of this invention, and their derivatives, may be used to block proteolysis of a target peptide in biochemical or cellular assays for ICE and ICE homologs or may be derivatized to bind to a stable resin as a tethered substrate for affinity chromatography applications. These and other uses which characterize commercial cysteine protease inhibitors will be evident to those of ordinary skill in the art.

The ICE inhibitors of this invention may be synthesized using conventional techniques. Advantageously, these compounds are conveniently synthesized from readily available starting materials.

The compounds of this invention are among the most readily synthesized ICE inhibitors known. Many of the previously described ICE inhibitors contain four or more chiral centers and numerous peptide linkages. The relative ease with which the compounds of this invention can be synthesized represents an advantage in the large scale production of these compounds.

For example, compounds of this invention may be prepared using the processes described herein. As can be appreciated by the skilled practitioner, these processes are not the only means by which the compounds described and claimed in this application may be synthesized. Further methods will be evident to those of ordinary skill in the art. Additionally, the various synthetic steps described herein may be performed in an alternate sequence or order to give the desired compounds.

A preferred method for preparing the compounds N-acylamino compounds of this invention comprises the steps of:

a) mixing a carboxylic acid with an N-alloc-protected amine in the presence of an inert solvent, triphenylphoshine, a nucleophilic scavenger, and tetrakis-triphenyl phosphine palladium(0) at ambient temperature under an inert atmosphere; and b) adding to the step a) mixture, HOBT and EDC; and optionally comprising the further step of:

c) hydrolyzing the step b) mixture in the presence of a solution comprising an acid and $H_2O$, wherein the step b) mixture is optionally concentrated, prior to hydrolyzing.

Preferably, the inert solvent is $CH_2Cl_2$, DMF, or a mixture of $CH_2Cl_2$ and DMF.

Preferably, the nucleophilic scavenger is dimedone, morpholine, trimethylsilyl dimethylamine, or dimethyl barbituric acid. More preferably, the nucleophilic scavenger is trimethylsilyl dimethylamine or dimethyl barbituric acid.

Preferably, the solution comprises trifluoroacetic acid in about 1–90% by weight. More preferably, the solution comprises trifluoroacetic acid in about 20–50% by weight.

Alternatively, the solution comprises hydrochloric acid in about 0.1–30% by weight. More preferably, the solution comprises hydrochloric acid in about 5–15% by weight.

More preferably, in the above process, the inert solvent is $CH_2Cl_2$, DMF, or a mixture of $CH_2Cl_2$ and DMF and the nucleophilic scavenger is dimedone, morpholine, trimethylsilyl dimethylamine, or dimethyl barbituric acid.

Most preferably, in the above process the inert solvent is $CH_2Cl_2$, DMF, or a mixture of $CH_2Cl_2$ and DMF and the nucleophilic scavenger is trimethylsilyl dimethylamine or dimethyl barbituric acid.

Preferably, the N-acylamino compound is a compound of this invention having the formula: (V):

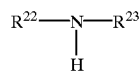
(V)

wherein:

$R^{22}$ is:

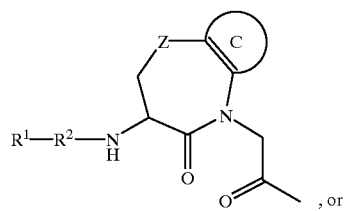
, or

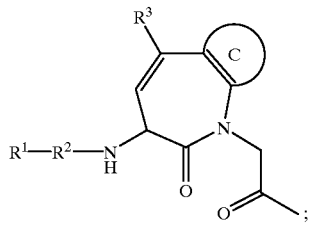
;

$R^{23}$ is:

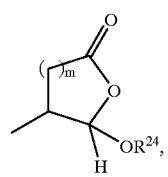
(x)

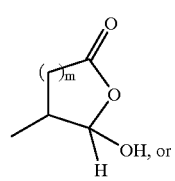
OH, or
(y)

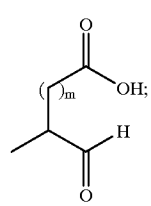
(z)

wherein m, in a preferred process, is 1;

$R^{24}$ is -alkyl, -cycloalkyl, -aryl, -heteroaryl, -alkylaryl, -alkylheteroaryl, or alkylheterocycle and the other substituents are as described above.

In these preferred processes the carboxylic acid is $R^{22}OH$ and the N-alloc protected amine is:

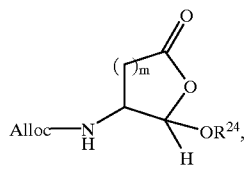

wherein $R^{24}$ is as defined above.

In order that this invention be more fully understood, the following examples are set forth. These examples are for the purpose of illustration only and are not to be construed as limiting the scope of the invention in any way.

EXAMPLE 1

Compounds 5a and 6a were prepared as described below.

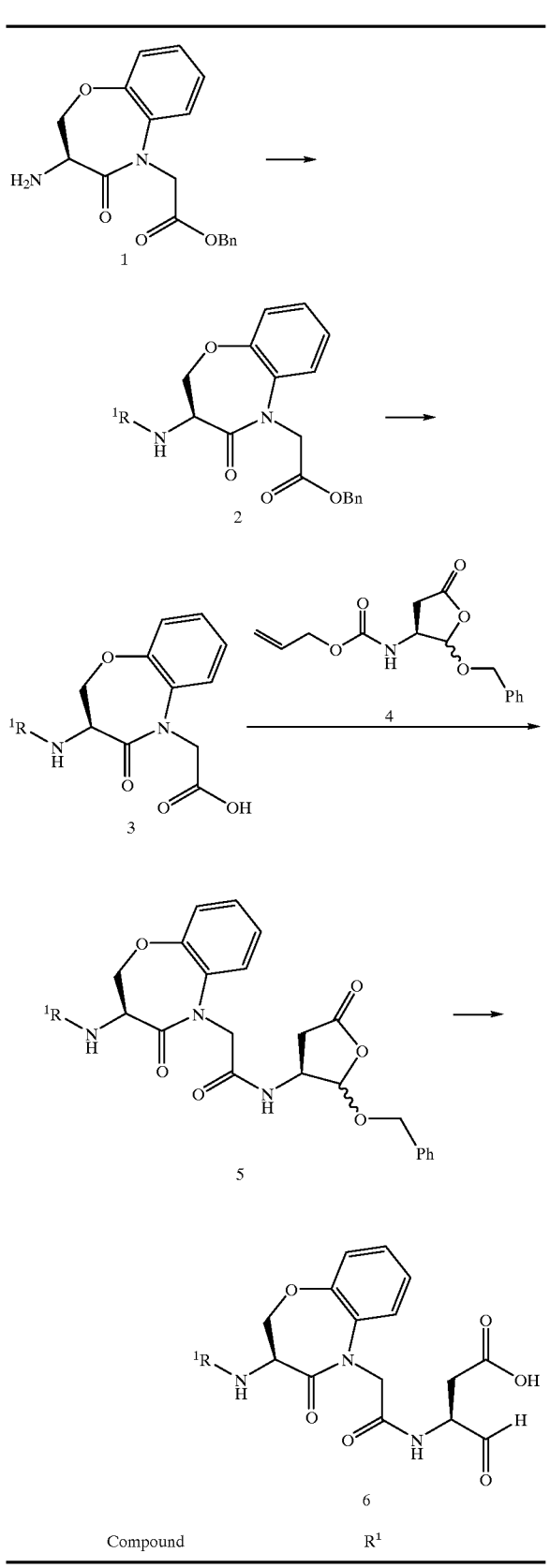

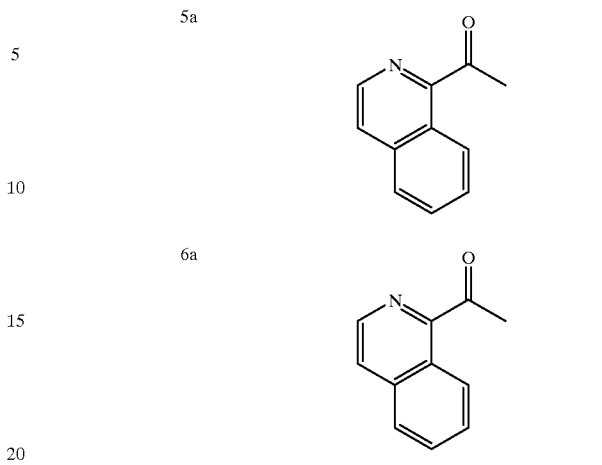

Benzyl 2-[(3S)-3-amino-4-oxo-2,3,4,5-tetrahydro-5H-1,5-benzoxazepin-5-yl]-ethanoate (1)

Was prepared by the methods described by Itoh et al., *Chem. Pharm. Bull.*, 34, p. 1128 (1996).

Benzyl 2-[(3S)-3-(isoquinolin-1-oyl)amino-4-oxo-2,3,4,5-tetrahydro-5H-1,5-benzoxazepin-5-yl]-ethanoate (2).

To a solution of Benzyl 2-[(3S)-3-amino-4-oxo-2,3,4,5-tetrahydro-5H-1,5-benzoxazepin-5-yl]-ethanoate hydrochloride 1 (1.277 g, 3.52 mmol) and isoquinoline-1-carboxylic acid (670 mg, 3.87 mmol) in 10 ml each of dimethylformamide (DMF) and dichloromethane ($CH_2Cl_2$) was added N-hydroxybenzotriazole, (523 mg, 3.87 mmol), 1-(3-dimethylaminopropyl)-3-ethylcarbodiimide hydrochloride (EDC) (880 mg, 4.58 mmol) and triethylamine ($Et_3N$) (1.2 ml, 8.8 mmol). The reaction was stirred at room temp. for 18 hrs. then diluted with ethyl acetate and washed with 10% $NaHSO_4$, sat. $NaHCO_3$, $H_2O$, and sat. NaCl. The organic layer was dried over anhydrous $Na_2SO_4$, filtered, and evaporated in vacuo to afford a gum that was purified by flash column chromatography eluting with 7/3 ($CH_2Cl_2$/EtOAc) to afford 1.56 g (79%) of the title compound.

2-[(3S)-3-(Isoquinolin-1-oyl)amino-4-oxo-2,3,4,5-tetrahydro-5H-1,5-benzoxazepin-5-yl]-ethanoic acid (3)

Benzyl $^2$-[(3S)-3-(isoquinolin-1-oyl)amino-4-oxo-2,3,4,5-tetrahydro-5H-1,5-benzoxazepin-5-yl]-ethanoate 2 (1.56 g, 2.78 mmol) and 500 mg of 10% Palladium on carbon were taken into 20 ml of methanol and charged with an hydrogen atmosphere and stirred for 3 hrs. The reaction was filtered through Celite and the filtrate evaporated in vacuo to afford 1.08 g (100%) of the title compound. The compound was used without further purification.

(3S)-3-(Isoquinolin-1-oyl)amino-4-oxo-2,3,4,5-tetrahydro-5H-1,5-benzoxazepine-N-[(2RS, 3S)-2-benzyloxy-5-oxo-tetrahydrofuran-3-yl]-5-acetamide (5a)

To a solution of 2-[(3S)-3-(Isoquinolin-1-oyl)amino-4-oxo-2,3,4,5-tetrahydro-5H-1,5-benzoxazepin-5-yl]-ethanoic acid 3, N-allyloxycarbonyl-4-amino-5-benzyloxy-2-oxotetrahydrofuran 4 (803 mg, 2.76 mmol) (Chapman, Bioorg. & Med. Chem. Letters 2, p. 613 (1992) and dimethylbarbituric acid (1.08 g, 6.9 mmol) in 10 ml of DMF and $CH_2Cl_2$ was added tetrakis(triphenylphosphine)palladium (0) (320 mg, 0.276 mmol), HOBT (286 mg, 2.12 mmol), and EDC (575 mg, 3 mmol). The reaction was stirred at room temp. for 18 hrs. then diluted with ethyl acetate and washed with 10% NaHSO$_4$, sat. NaHCO$_2$, and sat. NaCl. The organic layer was dried over anhydrous NaSO$_2$, filtered, and evaporated in vacuo to afford a gum that was purified by flash chromatography eluting with 7/3 (CH$_2$Cl$_2$/EtOAc) to afford 850 mg (69%) of the title compound as a white solid. $^1$H NMR (CDCl$_3$) δ2.2–2.32 (m, 1H), 2.58–2.62 (m, 0.5H), 2.9–2.98 (m, 0.5H), 4.2–4.52 (m, 2H), 4.59–4.65 (m, 1H), 4.75–4.98 (m, 4H), 5.06–5.14 (m, 0.5H), 5.16–5.22 (m, 0.5H), 5.45 (s, 0.5H), 5.54–5.58 (d, 0.5H), 7.00–7.41 (m, 10 H), 7.62–7.75 (m, 2H), 7.8–7.92 (m, 2H), 8.49–8.54 (d, 0.5H), 8.55–8.60 (d, 0.5H), 8.80–8.86 (d, 0.5H), 8.92–8.98 (d, 0.5H), 9.35–9.45 (m, 1H).

(3S)-3-[(3S)-3-(Isoquinolin-1-oyl)amino-4-oxo-2,3,4,5-tetrahydo-5H-1,5-benzoxazepine-5-acetylaminol-4-oxo-butyric acid (6a)

(3S)-3-(Isoquinolin-1-oyl)amino-4-oxo-2,3,4,5-tetrahydro-5H-1,5-benzoxazepine-N-[(2RS, 3S)-2-benzyloxy-5-oxo-tetrahydrofuran-3-yl]-5-acetamide (250 mg) was dissolved in 1 ml of acetonitrile (AcCN) and 10% HCl (10 ml) and stirred at room temp. for 2 hrs. The reaction was washed twice with 10 ml of diethyl ether (Et$_2$O). The combined ether washes were washed once with 15 ml of water and the combined water layers were diluted with acetonitrile and evaporated in vacuo to approximately 3 ml and triturated with Et$_2$O to afford a white precipitate that was collected and dried to give 118 mg (56%) of the title compound. $^1$H NMR (CD$_3$OD) δ2.43–2.51 (m, 1H), 2.64–2.72 (m, 1H), 4.23–4.39 (m, 2H), 4.46–4.52 (m, 1H), 4.58–4.64 (m, 1H), 4.73–4.82 (m, 2H), 5.24–5.3 (m, 1H), 7.27–7.48 (m, 4H), 7.83–7.89 (m, 1H), 7.96–8.02 (m, 1H), 8.12–8.17 (m, 1H), 8.22–8.28 (m, 1H), 8.55–8.60 (m, 1H), 8.91–8.96 (m, 1H).

EXAMPLE 2

Compounds 10a, 10b, 11a and 11b were prepared as described below.

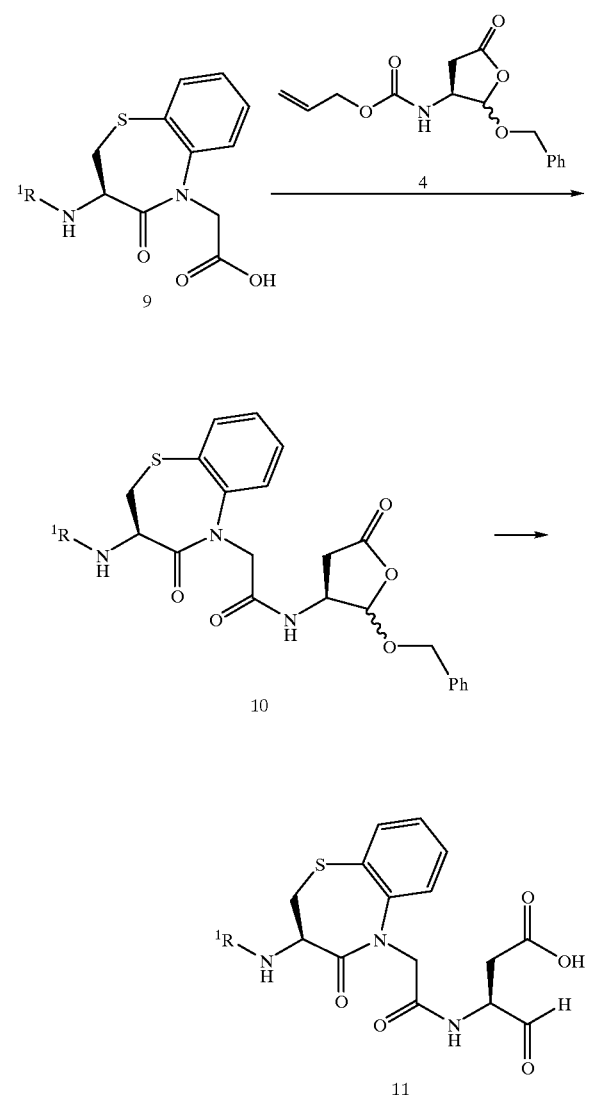

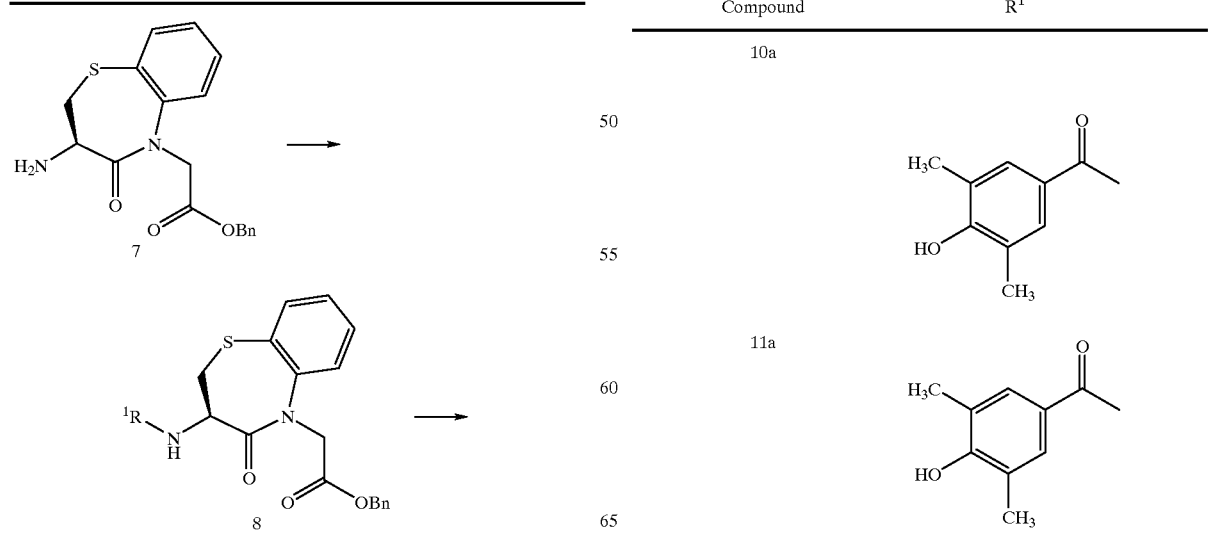

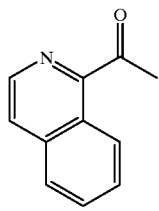

10b

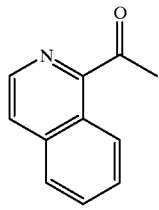

11b

Methyl 2-[(3S)-3-amino-4-oxo-2,3,4,5-tetrahydro-5H-1,5-benzothiazepin-1-yl]-ethanoate (7)

Was prepared by the methods described by Slade et al., *J. Med. Chem.* p. 1517 (1985)

Methyl 2-[(3S)-3-(3,5-dimethyl-4-hydroxybenzoyl) amino-4-oxo-2,3,4,5-tetrahydro-5H-1,5-benzothiazepin-1-yl]-ethanoate (8a)

Was prepared by the reaction of 7 and 3,5-dimethyl-4-hydroxybenzoic acid as reported in 2 to afford 1.83 g (78%) of the title compound.

2-[(3S)-3-(3,5-Dimethyl-4-hydroxybenzoyl)amino-4-oxo-2,3,4,5-tetrahydro-5H-1,5-benzothiazepin-1-yl]-ethanoic acid (9a)

To a solution of Methyl 2-[(3S)-3-(3,5-dimethyl-4-hydroxybenzoyl)amino-4-oxo-2,3,4,5-tetrahydro-5H-1,5-benzothiazepin-1-yl]-ethanoate 8a (1.8 g, 4.34 mmol) in 15 ml of methanol and 15 ml of THF was added 8.7 ml of 1N NaOH and the solution stirred for 18 hrs. at room temp. The mixture was evaporated to approximately 10 ml then diluted with 100 ml of water. The solution was acidified with 6N HCl and a precipitate resulted that was collected and dried to afford 1.64 g (94%) of the title compound as a white solid.

(3S)-3-(3,5-Dimethyl-4-hydroxybenzoyl)amino-4-oxo-2,3,4,5-tetrahydo-5H-1,5-benzothiazepine-N-((2RS, 3S)-2-benzyloxy-5-oxo-tetrahydrofuran-3-yl)-5-acetamide (10a)

Was synthesized from 4 and 9a by the method used to prepare 5 to afford 1.18 g (93%) of the title compound. $^1$H NMR (CDCl$_3$) δ1.68 (br. s, 1H), 2.24 (s, 3H), 2.31 (s, 3H), 2.41–2.48 (m, 0.5H), 2.51–2.62 (m, 0.5H), 2.64–2.73 (m, 0.5H), 2.95–3.04 (m, 1.5H), 3.56–3.65 (m, 0.5H), 3.85–3.92 (m, 0.5H), 4.31–4.57 (m, 1.5H), 4.58–4.74 (m, 1.5H), 4.75–4.95 (m, 3H), 5.57 (s, 0.5H), 5.62–5.67 (d, 0.5H), 6.77–6.84 (d, 0.5H), 6.88–6.95 (d, 0.5H), 7.22–7.44 (m, 7H), 7.45–7.61 (m, 2H), 7.62–7.78 (m, 2H), 7.81–7.91 (m, 1H).

(3S)-3-[(3S)-3-(3,5-Dimethyl-4-hydroxybenzoyl) amino-4-oxo-2,3,4,5-tetrahydro-5H-1,5-benzothiazepine-5-acetylamino]-4-oxo-butyric acid (11a)

Was synthesized from 10a by the methods used to prepare 6a to afford 200 mg (68%) of the title compound. $^1$H NMR (CD$_3$OD) δ2.21 (s, 6H), 2.43–2.54 (m, 1H), 2.58–2.79 (m, 1H), 3.10–3.28 (m, 1H), 3.63–3.71 (m, 1H), 4.18–4.42 (m, 2H), 4.48–4.82 (m, 3H), 7.28–7.38 (m, 1H), 7.40–7.61 (m, 6H), 7.67–7.75 (m, 1H).

Methyl 2-[(3S)-3-(isoquinolin-1-oyl)amino-4-oxo-2,3,4,5-tetrahydro-5H-1,5-benzothiazepin-1-yl]-ethanoate (8b)

Was prepared by the reaction of 7 and isoquinoline-1-carboxylic acid as reported in 2 to afford 1.43 g (96%) of the title compound.

2-[3-(3S)-3-(Isoquinolin-1-oyl)amino-4-oxo-2,3,4,5-tetrahydro-5H-1,5-benzothiazepin-1-yl]-ethanoic acid (9b)

Was prepared from 8b by the method reported for 9a to afford 1.32 g (95%) of the title compound.

(3S)-3-(Isoquinolin-1-oyl)amino-4-oxo-2,3,4,5-tetrahydo-5H-1,5-benzothiazepine-N-((2RS, 3S)-2-benzyloxy-5-oxo-tetrahydrofuran-3-yl)-5-acetamide (10b)

Was synthesized from 4 and 9b by the method used to prepare 5 to afford 1.65 g (85%) of the title compound as a white powder. $^1$H, NMR (CDCl$_3$) δ2.22–2.29 (m, 0.5 H, 2.38–2.44 (m, 0.5 H), 2.50–2.58 (m, 0.5H), 2.61–2.69 (m, 0.5H), 2.93–3.04 (m, 0.5H), 3.08–3.18 (m, 05.H), 3.50–3.62 (m, 0.5H), 3.88–3.98 (m, 0.5H), 4.3–4.55 (m, 1.5 H), 4.60–4.95 (m, 4.5H), 4.58 (s, 0.5H), 4.62–4.68 (d, 0.5H), 7.2–7.95 (m, 14H), 8.5–8.6 (m, 1H), 8.92–8.96 (d, 0.5H), 9.02–9.06 (d, 0.5H), 9.35–9.42 (m, 1H).

(3S)-3-[(3S)-4-Oxo-3-(isoquinolin-1-oyl)amino-4-oxo-2,3,4,5-tetrahydro-5H-1,5-benzoxazepine-5-acetylamino]-4-oxo-butyric acid (11b)

Was synthesized from 10b by the methods used to prepare 6 to afford 30 mg (37%) of the title compound as a white solid. $^1$H NMR (CD$_3$OD) δ2.42–2.5 (m, 1H), 2.6–2.72 (m, 1H), 3.15–3.27 (m, 1H), 3.83–3.92 (m, 1H), 4.25–4.42 (m, 2H), 4.62–4.68 (m, 1H), 4.75–4.95 (m, 2H), 7.38–7.45 (m, 1H), 7.55–7.65 (m, 2H), 7.70–7.85 (m, 3H), 7.95–8.10 (m, 2H), 8.50–8.58 (m, 1H), 9.02–9.08 (m, 1H).

EXAMPLE 3

Compounds 16a, 17a, 16b and 17b were prepared as described below.

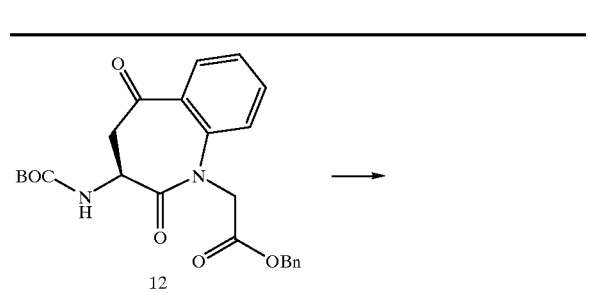

12

-continued

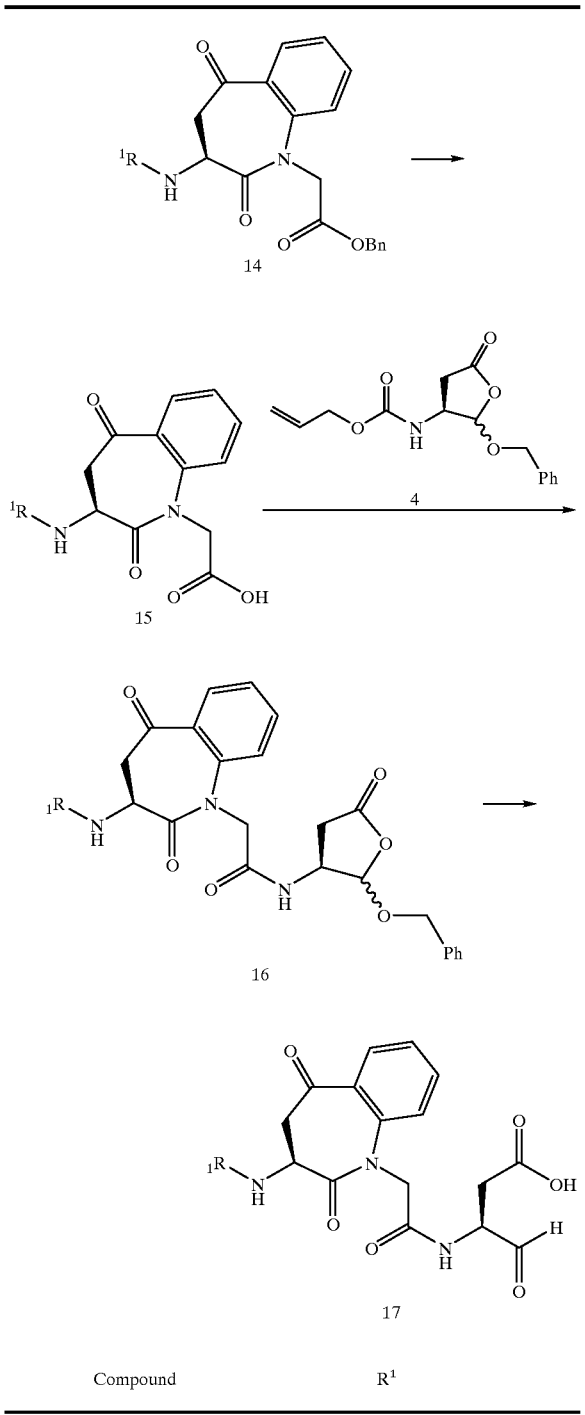

-continued

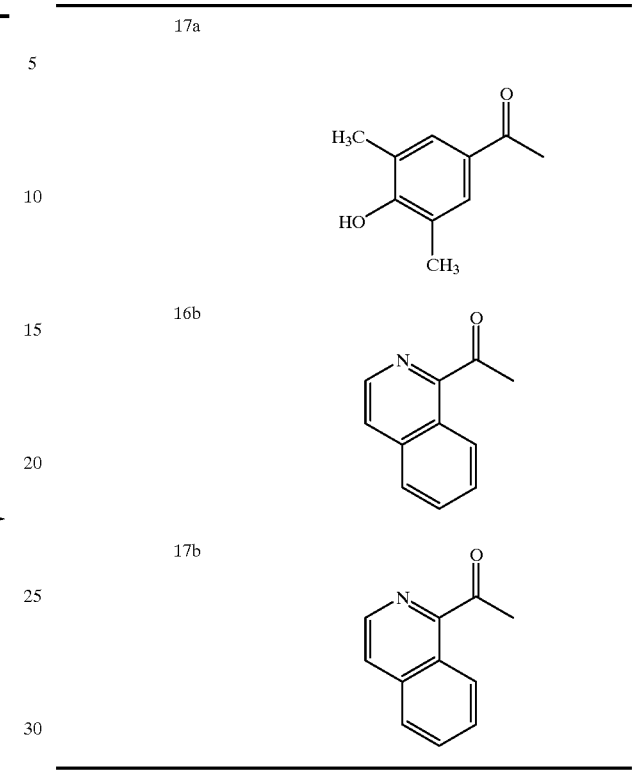

Benzyl 2-((3S)-2,5-dioxo-3-tert-butoxycarbonylamino-2,3,4, 5-tetrahydro-1H-1-benzazepin-1-yl)-ethanoate (12)

Was synthesized by the methods described by Ball et al., *J. Heterocyclic Chem.* 27, p. 279 (1990)

Benzyl 2-((3S)-2,5-dioxo-3-(3,5-dimethyl-4-hydroxybenzoyl)amino-2,3,4,5-tetrahydro-1H-1-benzazepin-1-yl)-ethanoate (14a)

Anhydrous HCl gas was bubbled into a solution of 12 (800 mg, 1.825 mmol) for 3 minutes then stirred at room temp. for 2 hrs. The solution was evaporated in vacuo to afford benzyl 2-((3S)-2,5-dioxo-3-amino-2,3,4,5-tetrahydro-1H-1-benzazepin-1-yl)-ethanoate hydrochloride 13a as a white solid.

To a solution of 13a and 3,5-dimethyl-4-hydroxybenzoic acid (307 mg, 1.85 mmol) in 5 ml each of DMF and $CH_2Cl_2$ was added HOBT (250 mg, 1.85 mmol), EDC (421 mg, 2.2 mmol), and triethylamine (0.64 ml, 4.56 mmol). The reaction was stirred at room temp. for 18 hrs. then diluted with EtOAc (150 ml) and washed with 10% $NaHSO_4$, sat. $NaHCO_3$ and sat. NaCl. The organic layer was dried over anhydrous $Na2SO_4$, filtered, and evaporated in vacuo to afford a gum that was purified by flash chromatography eluting with $CH_2Cl_2$/EtOAc (7/3) to afford 545 mg (62%) of the title compound.

2-((3S)-2,5-Dioxo-3-(3,5-dimethyl-4-hydroxybenzoyl)amino-2,3,4,5-tetrahydro-1H-1-benzazepin-1-yl)-ethanoic acid (15a)

Was prepared from 14a by the method reported for compound 3 to afford 500 mg (73%) of the title compound.

(3S)-2,5-Dioxo-3-(3,5-dimethyl-4-hydroxybenzoyl)amino-2,3,4,5-tetrahydo-1H-1-benzazepine-N-((2RS, 3S)-2-benzyloxy-5-oxo-tetrahydrofuran-3-yl)-1-acetamide (16a)

Was synthesized from 4 and 15a by the methods used to prepare 5 to afford 320 mg (39%) of the title compound. $^1$H

| Compound | R$^1$ |
|---|---|
| 16a | 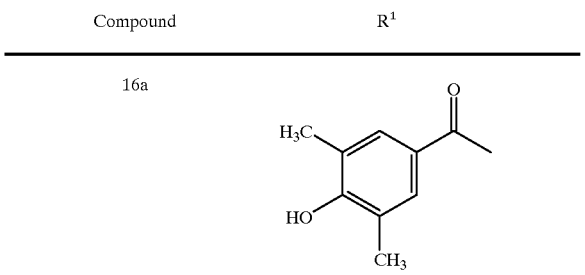 |

NMR (CDCl$_3$) δ2.23 (s, 3H), 2.24 (s, 3H), 2.40–2.47 (m, 0.5H), 2.52–2.60 (m, 0.5H), 2.85–3.13 (m, 2H), 3.33–3.48 (m, 1H), 4.2–4.32 (m, 1H), 4.48–4.64 (m, 3H), 4.75– 4.91 (m, 2H), 5.31–5.38 (m, 1H), 5.42 (s, 0.5H), 5.55–5.60 (d, 0.5H) , 6.63–6.71 (d, 0.5H) , 7.05–7.12 (d, 0.5H), 7.12–7.17 (d, 0.5H), 7.22–7.74 (m, 12.5H).

(3S)-3-[(3S)-2,5-Dioxo-3-(3,5-dimethyl-4-hydroxybenzoyl)amino-2,3,4, 5-tetrahydro-1H-1-benzazepine-1-acetylamino]-4-oxo-butyric acid (17a)

Was synthesized from 16a by the methods used to prepare 6 to afford 121 mg (72%) of the title compound. 1H NMR (CD$_3$OD) δ2.25 (s, 6H), 2.39–2.52 (m, 1H), 2.55–2.72 (m, 1H), 3.12–3.30 (m, 2H), 4.21–4.32 (m, 1H), 4.40–4.61 (m, 3H), 5.23–5.34 (m, 1H), 7.34–7.53 (m, 4H), 7.58–7.70 (m, 2H).

Benzyl 2-((3S)-2,5-dioxo-3-(isoquinolin-1-oyl) amino-2,3,4,5-tetrahydro-1H-1-benzazepin-1-yl)-ethanoate (14b)

Was prepared by the method reported in 14a by reaction of 12 and isoquinoline-1-carboxylic acid to afford 930 mg (92%) of the title compound.

2-((3S)-2,5-dioxo-3-(isoquinolin-1-oyl)amino-2,3,4, 5-tetrahydro-1H-1-benzazepin-1-yl)-ethanoic acid (15b)

Was prepared from 14a by the method used to prepare 3 to afford 568 m g (100%) of the title compound.

(3S)-2,5-Dioxo-3-(Isoquinolin-3-oyl)amino-2,3,4,5-tetrahyo-1H-1-benzazepine-N-((2RS, 3S)-2-benzyloxy-5-oxo-tetrahydrofuran-3-yl)-1-acetamide (16b)

Was synthesized from 15b by the methods used to prepare 5 to afford 425 mg (52%) of title compound as a white powder. $^1$H NMR (CDCl$_3$) δ2.52–2.62 (m, 1H), 2.82–2.92 (m, 0.5H) 2.96–3.21 (m, 1.5H), 3.39–3.51 (m, 1H), 4.05–4.26 (m, 1H), 4.45–4.69 (m, 2H), 4.72–4.90 (m, 2H), 5.32–5.45 (m, 1H), 5.49 (s, 0.5H), 5.52–5.58 (d, 0.5H), 6.72–6.80 (d, 0.5H), 6.98–7.08 (m, 0.5H), 7.21–7.88 (m, 13H), 8.42–8.47 (d, 0.5H), 8.48–8.53 (d, 0.5H), 9.01–9.19 (m, 1H), 9.36–9.46 (m, 1H).

(3S)-3-[(3S)-2,5-Dioxo-3-(isoquinolin-1-oyl)amino-2,3,4,5-tetrahydro-1H-1-benzazopine-1-acetylamino]-4-oxo-butyric acid. (17b)

Was synthesized from 16b by the methods used to prepare 6 to afford 37 mg (16%) of the title compound as a white powder. $^1$H NMR (CD$_3$OD) δ2.41–2.80 (m, 2H), 3.21–3.42 (m, 1H), 3.49–3.65 (m, 0.5H), 3.82–3.96 (m, 0.5H), 4.25–4.63 (m, 3H), 5.03–5.48 (m, 2H), 7.40–7.58 (m, 2H), 7.62–7.85 (m, 4H), 7.92–8.05 (m, 2H), 8.50–8.58 (d, 1H), 9.09–9.21 (m, 1H).

EXAMPLE 4

ICE Inhibition

We obtained inhibition constants ($K_i$) and IC$_{50}$ values for compounds of this invention using the methods described in Examples 5 and 9. Table 1 lists data for selected compounds of this invention.

TABLE 1

| Compound | UV-Visible $K_i$ (nM) | Whole human blood IC50 (nM) |
|---|---|---|
| 17a | 12 | 3200 |
| 11a | 7.5 | 8800 |
| 17b | 45 | >20000 |
| 11b | 14 | 19000 |
| 6a | 22 | >20000 |

EXAMPLE 5

1. Enzyme Assay with UV-visible Substrate

This assay is run using an Succinyl-Tyr-Val-Ala-Asp-p-Nitroanilide substrate. Synthesis of analogous substrates is described by L. A. Reiter (*Int. J. Peptide Protein Res.,* 43, pp. 87–96 (1994)). The assay mixture contains:

65 μl buffer (10 mM Tris, 1 mM DTT, 0.1% CHAPS @ pH 8.1)
10 μl ICE (50 nM final concentration to give a rate of ~1 mOD/min)
5 μl DMSO/Inhibitor mixture
20 μl 400 μM Substrate (80 μM final concentration)
100 μl total reaction volume The visible ICE assay is run in a 96-well microtiter plate. Buffer, ICE and DMSO (if inhibitor is present) are added to the wells in the order listed. The components are left to incubate at room temperature for 15 minutes starting at the time that all components are present in all wells. The microtiter plate reader is set to incubate at 37° C. After the 15 minute incubation, substrate is added directly to the wells and the reaction is monitored by following the release of the chromophore (pNA) at 405–603 nm at 37° C. for 20 minutes. A linear fit of the data is performed and the rate is calculated in mOD/min. DMSO is only present during experiments involving inhibitors, buffer is used to make up the volume to 100 μl in the other experiments.

2. Enzyme Assay with Fluorescent Substrate

This assay is run essentially according to Thornberry et al., *Nature,* 356, pp. 768–774 (1992), using substrate 17 referenced in that article. The substrate is: Acetyl-Tyr-Val-Ala-Asp-amino-4-methylcoumarin (AMC). The following components are mixed:

65 μl buffer (10 nM Tris, 1 mM DTT, 0.1% CHAPS @ pH8.1)
10 μl ICE (2–10 nM final concentration)
5 μl DMSO/inhibitor solution
20 μl 150 μM Substrate (30 μM final)
100 μl total reaction volume The assay is run in a 96-well microtiter plate. Buffer and ICE are added to the wells. The components are left to incubate at 37° C. for 15 minutes in a temperature-controlled wellplate. After the 15 minute incubation, the reaction is started by adding substrate directly to the wells and the reaction is monitored at 37° C. for 30 minutes by following the release of the AMC fluorophore using an excitation wavelength for 380 nm and an emission wavelength of 460 nm. A linear fit of the data for each well is performed and a rate is determined in fluorescence units per second.

For determination of enzyme inhibition constants ($K_i$) or the mode of inhibition (competitive, uncompetitive or noncompetitive), the rate data determined in the enzyme assays at varying inhibitor concentrations are computer-fit to standard enzyme kinetic equations (see I. H. Segel, *Enzyme Kinetics,* Wiley-Interscience, 1975).

The determination of second order rate constants for irreversible inhibitors was performed by fitting the fluorescence vs time data to the progress equations of Morrison. Morrison, J. F., *Mol. Cell. Biophys.*, 2, pp. 347–368 (1985). Thornberry et al. published a description of these methods for measurement of rate constants of irreversible inhibitors of ICE. Thornberry, N. A., et al. Biochemistry, 33, pp. 3923–3940 (1994). For compounds where no prior complex formation can be observed kinetically, the second order rate constants ($k_{inact}$) are derived directly from the slope of the linear plots of $k_{obs}$ vs. inhibitor concentration [I]. For compounds where prior complex formation to the enzyme can be detected, the hyperbolic plots of $k_{obs}$ vs. [I] are fit to the equation for saturation kinetics to first generate $K_i$ and k'. The second order rate constant $k_{inact}$ is then given by $k'/K_i$.

3. PBMC Cell Assay

IL-1β Assay with a Mixed Population of Human Peripheral Blood Mononuclear Cells (PBMC) or Enriched Adherent Mononuclear Cells Processing of pre-IL-1β by ICE can be measured in cell culture using a variety of cell sources. Human PBMC obtained from healthy donors provides a mixed population of lymphocyte subtypes and mononuclear cells that produce a spectrum of interleukins and cytokines in response to many classes of physiological stimulators. Adherent mononuclear cells from PBMC provides an enriched source of normal monocytes for selective studies of cytokine production by activated cells.

Experimental Procedure

An initial dilution series of test compound in DMSO or ethanol is prepared, with a subsequent dilution into RPMI-10% FBS media (containing 2 mM L-glutamine, 10 mM HEPES, 50 U and 50 ug/ml pen/strep) respectively to yield drugs at 4×the final test concentration containing 0.4% DMSO or 0.4% ethanol. The final concentration of DMSO is 0.1% for all drug dilutions. A concentration titration which brackets the apparent $K_i$ for a test compound determined in an ICE inhibition assay is generally used for the primary compound screen.

Generally 5–6 compound dilutions are tested and the cellular component of the assay is performed in duplicate, with duplicate ELISA determinations on each cell culture supernatant.

PBMC Isolation and IL-1 Assay

Buffy coat cells isolated from one pint human blood (yielding 40–45 ml final volume plasma plus cells) are diluted with media to 80 ml and LeukoPREP separation tubes (Becton Dickinson) are each overlaid with 10 ml of cell suspension. After 15 min centrifugation at 1500–1800× g, the plasma/media layer is aspirated and then the mononuclear cell layer is collected with a Pasteur pipette and transferred to a 15 ml conical centrifuge tube (Corning). Media is added to bring the volume to 15 ml, gently mix the cells by inversion and centrifuge at 300×g for 15 min. The PBMC pellet is resuspended in a small volume of media, the cells are counted and adjusted to $6 \times 10^6$ cells/ml.

For the cellular assay, 1.0 ml of the cell suspension is added to each well of a 24-well flat bottom tissue culture plate (Corning), 0.5 ml test compound dilution and 0.5 ml LPS solution (Sigma #L-3012; 20 ng/ml solution prepared in complete RPMI media; final LPS concentration 5 ng/ml). The 0.5 ml additions of test compound and LPS are usually sufficient to mix the contents of the wells. Three control mixtures are run per experiment, with either LPS alone, solvent vehicle control, and/or additional media to adjust the final culture volume to 2.0 ml. The cell cultures are incubated for 16–18 hr at 37° C. in the presence of 5% $CO_2$.

At the end of the incubation period, cells are harvested and transferred to 15 ml conical centrifuge tubes. After centrifugation for 10 min at 200×g, supernatants are harvested and transferred to 1.5 ml Eppendorf tubes. It may be noted that the cell pellet may be utilized for a biochemical evaluation of pre-IL-1β and/or mature IL-1β content in cytosol extracts by Western blotting or ELISA with pre-IL-1β specific antisera.

Isolation of Adherent Mononuclear Cells

PBMC are isolated and prepared as described above. Media (1.0 ml) is first added to wells followed by 0.5 ml of the PBMC suspension. After a one hour incubation, plates are gently shaken and nonadherent cells aspirated from each well. Wells are then gently washed three times with 1.0 ml of media and final resuspended in 1.0 ml media. The enrichment for adherent cells generally yields $2.5–3.0 \times 10^5$ cells per well. The addition of test compounds, LPS, cell incubation conditions and processing of supernatants proceeds as described above.

ELISA

We have used Quantikine kits (R&D Systems) for measurement of mature IL-1β. Assays are performed according to the manufacturer's directions. Mature IL-1β levels of about 1–3 ng/ml in both PBMC and adherent mononuclear cell positive controls are observed. ELISA assays are performed on 1:5, 1:10 and 1:20 dilutions of supernatants from LPS-positive controls to select the optimal dilution for supernatants in the test panel.

The inhibitory potency of the compounds can be represented by an $IC_{50}$ value, which is the concentration of inhibitor at which 50% of mature IL-1β is detected in the supernatant as compared to the positive controls.

The skilled practitioner realizes that values obtained in cell assays, such as those described herein, can depend on multiple factors. The values may not necessarily represent fine quantitative results.

EXAMPLE 6

In vivo Bioavailability Determination

The drugs (10–100 mg/kg) were dosed orally to rats (10 mL/kg) in ethanol/PEG/water, β-cyclodextrin, labrosol/water or cremophor/water. Blood samples were drawn from the carotid artery at 0.25, 0.50, 1, 1.5, 2, 3, 4, 6, and 8 hours after dosing, centrifuged to separate plasma and stored at −70° C. until analyzed. Aldehyde concentrations were determined using HPLC/MS. Pharmacokinetic analysis of data was performed by non-linear regression using RStrip (MicroMath Software, UT). Drug availability values may be determined as follows: (AUC of drug after oral prodrug dosing/AUC of drug after i.v. dosing of drug)×(dose i.v./dose p.o.)×100%.

Results in Table 2 show that prodrugs 16b give significant blood levels of drug when dosed orally.

TABLE 2

Oral Bioavailability of 16b in Rat.

| Compound | Dose (mg/kg) | Cmax (µg/ml) |
|---|---|---|
| 16b | 50 | 6.1 |

EXAMPLE 7

Pharmacokinetic Studies in the Mouse

Peptidyl ICE inhibitors are cleared rapidly with clearance rates greater than 100 µg/min/kg. Compounds with lower clearance rates have improved pharmacokinetic properties relative to peptidyl ICE inhibitors.

Clearance rates for compounds of this invention (μg/min/kg) may be obtained using the method described below:

Sample Preparation and Dosing

Compounds are dissolved in sterile TRIS solution (0.02M or 0.05M) at a concentration of 2.5 mg/ml. Where necessary to ensure a complete solution, the sample is first dissolved in a minimum of dimethylacetamide (maximum of 5% of total solution volume) then diluted with the TRIS solution.

The drug solution is administered to CD-1 mice (Charles River Laboratories—26–31 g) via the tail vein at a dose volume of 10 ml/kg giving a drug dose of 25 mg/kg, for example.

Mice may be dosed in groups (of 5, for example) for each timepoint (generally from 2 minutes to 2 hours) and then at the appropriate time the animals are anesthetized with halothane and the blood collected into individual heparinized tubes by jugular severance. The blood samples are cooled to 0° C. then the plasma separated and stored at −20° C. until assayed.

Bioassay

Drug concentration in the plasma samples are determined by HPLC analysis with UV or MS (ESP) detection. Reverse phase chromatography is employed using a variety of bonded phases from C1 to C18 with eluents composed of aqueous buffer/acetonitrile mixtures run under isocratic conditions.

Quantitation is by external standard methods with calibration curves constructed by spiking plasma with drug solutions to give concentrations in the range of 0.5 to 50 μg/ml.

Prior to analysis the plasma samples are deproteinated by the addition of acetonitrile, methanol, trichloroacetic acid or perchloric acid followed by centrifugation at 10,000 g for 10 minutes. Sample volumes of 20 μl to 50 μl are injected for analysis.

Representative Dosing and Sampling Procedure

The drug is dissolved in sterile 0.02M Tris to give a 2.5 mg/ml solution which is administered to 11 groups of 5 male CD-1 mice via the tail vein at a dose of 25 mg/kg. At each of the following timepoints: 2, 5, 10, 15, 20, 30, 45, 60, 90 and 120 minutes a group of animals is anaesthetised and the blood collected into heparinized tubes. After separation the plasma is stored at −20° C. until assayed.

Representative Assay

Aliquots of plasma (150 μl) are treated with 5% perchloric acid (5 μl) then mixed by vortexing and allowing to stand for 90 minutes prior to centrifugation. The resulting supernatant is separated and 20 μl is injected for HPLC analysis.

| Representative HPLC Conditions | | |
|---|---|---|
| Column | 100 × 4.6 mm | Kromasil KR 100 5C4 |
| Mobile Phase 0. | 1 m Tris pH 7.5 | 86% |
| | Acetonitrile | 14% |
| Flowrate | 1 ml/min | |
| Detection | UV at 210 nm | |
| Retention Time | 3.4 mins | |

EXAMPLE 8

Peptidyl ICE inhibitors are cleared rapidly with clearance rates greater than 80 ml/min/kg. Compounds with lower clearance rates have improved pharmacokinetic properties relative to peptidyl ICE inhibitors.

The rate of clearance in the rat (ml/min/kg) for compounds of this invention may be obtained using the method described below:

In vivo Rat Clearance Assay

Representative Procedure

Cannulations of the jugular and carotid vessels of rats under anesthesia are performed one day prior to the pharmacokinetic study. M. J. Free, R. A. Jaffee; 'Cannulation techniques for the collection blood and other bodily fluids'; in: Animal Models; p. 480–495; N. J. Alexander, Ed.; Academic Press; (1978). Drug (10 mg/mL) is administered via the jugular vein in a vehicle usually consisting of: propylene glycol/saline, containing 100 mM sodium bicarbonate in a 1:1 ratio. Animals are dosed with 10–20 mg drug/kg and blood samples are drawn at 0, 2, 5, 7, 10, 15, 20, 30, 60, and 90 minutes from an indwelling carotid catheter. The blood is centrifuged to plasma and stored at −20° C. until analysis. Pharmacokinetic analysis of data is performed by non-linear regression using standard software such as RStrip (MicroMath Software, UT) and/or Pcnonlin (SCI Software, NC) to obtain clearance values.

Representative Analytical

Rat plasma is extracted with an equal volume of acetonitrile (containing 0.1% TFA). Samples are then centrifuged at approximately 1,000×g and the supernatant analyzed by gradient HPLC. A typical assay procedure is described below.

200 μL of plasma is precipitated with 200 μL of 0.1% trifluoroacetic acid (TFA) in acetonitrile and 10 μL of a 50% aqueous zinc chloride solution, vortexed then centrifuged at ~1000×g and the supernatant collected and analyzed by HPLC.

| HPLC procedure: | |
|---|---|
| Column: | Zorbax SB-CN (4.6 × 150 mm) (5μ particle size) |
| Column temperature: | 50° C. |
| Flow rate: | 1.0 mL/min |
| Injection volume: | 75 μL. |
| Mobile phase: | A is 0.1% TFA in water and B is 100% acetonitrile |
| Gradient employed: | 100% A to 30% A in 15.5 min 0% A at 16 min 100% A at 19.2 min |
| Wavelength: | 214 nm |

A standard curve is run at 20, 10, 5, 2 and 1 μg/mL concentrations.

EXAMPLE 9

Whole Blood Assay for IL-1β Production

Whole blood assay $IC_{50}$ values for compounds of this invention were obtained using the method described below:

Purpose

The whole blood assay is a simple method for measuring the production of IL-1β (or other cytokines) and the activity of potential inhibitors. The complexity of this assay system, with its full complement of lymphoid and inflammatory cell types, spectrum of plasma proteins and red blood cells is an ideal in vitro representation of human in vivo physiologic conditions.

Materials

Pyrogen-free syringes (~30 cc)

Pyrogen-free sterile vacuum tubes containing lyophilized $Na_2EDTA$ (4.5 mg/10 ml tube)

Human whole blood sample (~30–50 cc)
1.5 ml Eppendorf tubes
Test compound stock solutions (~25 mM in DMSO or other solvent)
Endotoxin-free sodium chloride solution (0.9%) and HBSS
Lipopolysaccharide (Sigma; Cat. # L-3012) stock solution at 1 mg/ml in HBSS
IL-1β ELISA Kit (R & D Systems; Cat # DLB50)
TNFα ELISA Kit (R & D Systems; Cat # DTA50)
Water bath or incubator
Whole Blood Assay Experimental Procedure Set incubator or water bath at 30° C. Aliquot 0.25 ml of blood into 1.5 ml eppendorf tubes. Note: be sure to invert the whole blood sample tubes after every two aliquots. Differences in replicates may result if the cells sediment and are not uniformly suspended. Use of a positive displacement pipette will also minimize differences between replicate aliquots.

Prepare drug dilutions in sterile pyrogen-free saline by serial dilution. A dilution series which brackets the apparent $K_i$ for a test compound determined in an ICE inhibition assay is generally used for the primary compound screen. For extremely hydrophobic compounds, prepare compound dilutions in fresh plasma obtained from the same blood donor or in PBS-containing 5% DMSO to enhance solubility.

Add 25 μl test compound dilution or vehicle control and gently mix the sample. Then add 5.0 μl LPS solution (250 ng/ml stocked prepared fresh: 5.0 ng/ml final concentration LPS), and mix again. Incubate the tubes at 30° C. in a water bath for 16–18 hr with occasional mixing. Alternatively, the tubes can be placed in a rotator set at 4 rpm for the same incubation period. This assay should be set up in duplicate or triplicate with the following controls: negative control—no LPS; positive control—no test inhibitor; vehicle control—the highest concentration of DMSO or compound solvent used in the experiment. Additional saline is added to all control tubes to normalize volumes for both control and experimental whole blood test samples.

After the incubation period, whole blood samples are centrifuged for 10 minutes at ~2000 rpm in the microfuge, plasma is transferred to a fresh microfuge tube and centrifuged at 1000xg to pellet residual platelets if necessary. Plasma samples may be stored frozen at −70° C. prior to assay for cytokine levels by ELISA.
ELISA R & D Systems (614 McKinley Place N.E. Minneapolis, Minn. 55413) Quantikine kits may be used for measurement of IL-1β and TNF-α. The assays are performed according to the manufacturer's directions. IL-1β levels of ~1–5 ng/ml in positive controls among a range of individuals may be observed. A 1:200 dilution of plasma for all samples is usually sufficient for experiments for ELISA results to fall on the linear range of the ELISA standard curves. It may be necessary to optimize standard dilutions if you observe differences in the whole blood assay. Nerad, J. L. et al., *J. Leukocyte Biol.*, 52, pp. 687–692 (1992).

EXAMPLE 10

Inhibition of ICE Homologs

1. Isolation of ICE homologs

Expression of TX in insect cells using a baculovirus expression system

TX cDNA (C. Faucheu et al., *EMBO*, 14, p. 1914 (1995)) is subcloned into a modified pVL1393 transfer vector, co-transfected the resultant plasmid (pVL1393/TX) into insect cells with viral DNA and the recombinant baculovirus is identified. After the generation of high titer recombinant virus stock, the medium is examined for TX activity using the visible ICE assay. Typically, infection of Spodoptera frugiperda (Sf9) insect cells at an MOI of 5 with recombinant virus stock result in a maximum expression after 48 hours of 4.7 μg/ml. ICE is used as a standard in the assay.

Amino terminal T7 tagged versions of ICE or TX are also expressed. Designed originally to assist the identification and purification of the recombinant proteins, the various constructs also allow examination of different levels of expression and of the relative levels of apoptosis experienced by the different homologs. Apoptosis in the infected Sf9 cells (examined using a Trypan Blue exclusion assay) is increased in the lines expressing ICE or TX relative to cells infected with the viral DNA alone.

Expression and Purification of N-terminally $(His)_6$-tagged CPP32 in *E. coli*

A cDNA encoding a CPP32 (Alnemri et al, 1994) polypeptide starting at Ser (29) is PCR amplified with primers that add in frame XhoI sites to both the 5' and 3' ends of the cDNA and the resulting XhoI fragment ligated into a Xho I-cut pET-15b expression vector to create an in frame fusion with $(his)_6$ tag at the N-terminus of the fusion protein. The predicted recombinant protein starts with the amino acid sequence of MGSSHHHHHHSSGLVPRGSHMLE, where LVPRGS represents a thrombin cleavage site, followed by CPP32 starting at Ser (29). *E. coli* BL21(DE3) carrying the plasmid are grown to log phase at 30° C. and are then induced with 0.8 mM IPTG. Cells are harvested two hours after IPTG addition. Lysates are prepared and soluble proteins are purified by Ni-agarose chromatography. All of the expressed CPP32 protein would be in the processed form. N-terminal sequencing analysis should indicate that the processing has occurred at the authentic site between Asp (175) and Ser (176). Approximately 50 μg of CPP32 protein from 200 ml culture could be obtained. As determined by active site titration, the purified proteins are fully active. The protease preparations are also very active in vitro in cleaving PARP as well as the synthetic DEVD-AMC substrate (Nicholson et al., 1995).

2. Inhibition of ICE Homologs

The selectivity of a panel of reversible inhibitors for ICE homologs may be obtained. ICE enzyme assays are performed according to Wilson et al. (1994) using a YVAD-AMC substrate (Thornberry et al., 1992). Assay of TX activity is performed using the ICE substrate under identical conditions to ICE. Assay of CPP32 is performed using a DEVD-AMC substrate (Nicholson et al., 1995).

Second-order rate constants for inactivation of ICE and ICE homologs with selected irreversible inhibitors are obtained.

EXAMPLE 11

Inhibition of Apoptosis

Fas-Induced Apoptosis in U937 Cells

Compounds may be evaluated for their ability to block anti-Fas-induced apoptosis. Using RT-PCR, mRNA encoding ICE, TX, ICH-1, CPP32 and CMH-1 in unstimulated U937 cells may be detected. This cell line may be used for apoptosis studies. For example, U937 cells are seeded in culture at $1 \times 10^5$ cells/ml and grown to $~5 \times 10^6$ cells/ml. For apoptosis experiments, 2×10⁶ cells are plated in 24-well tissue culture plates in 1 ml RPMI-1640–10% FBS and stimulated with 100 ng/ml anti-Fas antigen antibody (Medical and Biological Laboratories, Ltd.). After a 24 hr incubation at 37° C., the percentage of apoptotic cells is determined by FACS analysis using ApoTag reagents.

All compounds are tested initially at 20 μm and titrations are performed with active compounds to determine $IC_{50}$ values.

EXAMPLE 12

In vivo Acute Assay for Efficacy as Anti-inflammatory Agent

LPS-Induced IL-1β Production

Efficacy is evaluated in CD1 mice (n is 6 per condition, for example) challenged with LPS (20 mg/kg IP). The test compounds are prepared in olive oil:DMSO:ethanol (90:5:5) and administered by IP injection one hour after LPS. Blood is collected seven hours after LPS challenge. Serum IL-1β levels are measured by ELISA.

Compounds may also be administered by oral gavage to assess absorption. Compounds administered orally that inhibit IL-1β secretion are suggestive of the potential oral efficacy of those compounds as ICE inhibitors and thus as anti-inflammatory agents.

EXAMPLE 13

Measurement of Blood Levels of Prodrugs

Mice are administered a p.o. (oral) dose of compounds (50 mg/kg, for example) prepared in 0.5 % carboxymethyl-cellulose. Blood samples are collected at 1 and 7 hours after dosing. Serum is extracted by precipitation with an equal volume of acetonitrile containing 2 % formic acid followed by centrifugation. The supernatant is analyzed by liquid chromatography-mass spectrometry (ESI-MS) with a detection level of 0.03 to 3 μg/ml. Detectable blood levels are thus determined.

EXAMPLE 14

ICE Inhibition Assays—IGIF

IGIF may be substituted for IL-1 in the ICE inhibition assays described in Example 5. Thus, the ability of ICE inhibitors to decrease IGIF production may be determined.

For example, to run the human PBMC assay, human buffy coat cells may be obtained from blood donors and peripheral blood mononuclear cells (PBMC) isolated by centrifugation in LeukoPrep tubes (Becton-Dickinson, Lincoln Park, N.J.). PBMC are added (3×10⁶/well) to 24 well Corning tissue culture plates and after 1 hr incubation at 37° C., non-adherent cells are removed by gently washing. Adherent mononuclear cells are stimulated with LPS (1 μg/ml) with or without ICE inhibitor in 2 ml RPMI-1640–10% FBS. After 16–18 hr incubation at 37° C., IGIF and IFN- are quantitated in culture supernatants by ELISA.

EXAMPLE 15

The antiviral efficacy of compounds may be evaluated in various in vitro and in vivo assays. For example, compounds may be tested in in vitro viral replication assays. In vitro assays may employ whole cells or isolated cellular components. In vivo assays include animal models for viral diseases. Examples of such animal models include, but are not limited to, rodent models for HBV or HCV infection, the Woodchuck model for HBV infection, and chimpanzee model for HCV infection.

ICE inhibitors may also be evaluated in animal models for dietary alcohol-induced disease.

EXAMPLE 16

Compounds 5c and 6c, were prepared by methods similar to the methods used to prepare compounds 5a and 6a.

Compound 18a and 19a were prepared by methods similar to the methods used to prepare compounds 10a, 10b, 11a and 11b.

The structures of compounds 5c, 6c, 18a and 19a are shown in Table 3.

TABLE 3

| Example | Structure |
|---------|-----------|
| 5c | 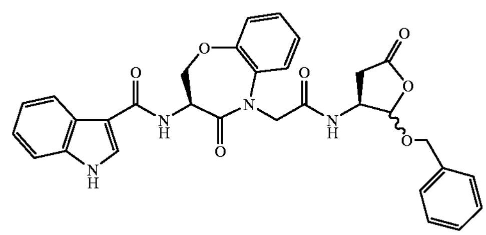 |
| 6c | 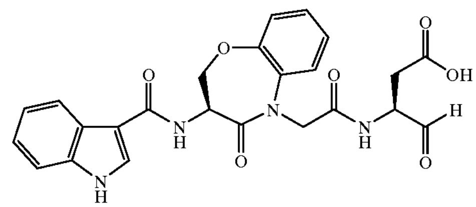 |
| 18a | 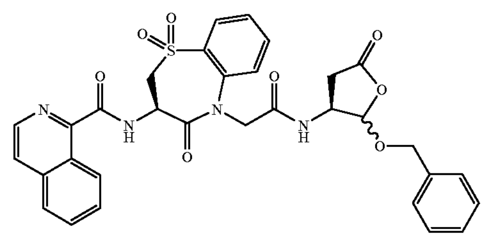 |
| 19a | 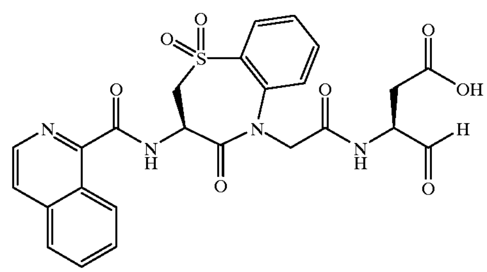 |

EXAMPLE 17

ICE Inhibition

We obtained inhibition constants ($K_i$) and $IC_{50}$ values for compounds of this invention using the methods described in Examples 5 and 9. Table 4 lists data for selected compounds of this invention.

47

TABLE 4

| Compound | UV-Visible Ki (nM) | Cell PBMC avg. IC50 (nM) | Whole human blood IC50 (nM) |
|---|---|---|---|
| 19a | 140 | 770 | 9500 |
| 6c | 20 | 650 | >20000 |
| 17b | 45 | 1720 | >20000 |
| 11b | 14 | 800 | 19000 |
| 6a | 22 | 1000 | >20000 |

EXAMPLE 18

We obtained inhibition data in Table 5 using the methods described in Example 12. Efficacy for Prodrugs in LPS-Induced IL-1β Production in Mice. Time of compound administration relative to time of LPS challenge was 1 hour. Dose of compound was PO @ 100 mg/kg.

TABLE 5

| Compound | % Inhibition of IL-1β |
|---|---|
| 16b | 53% |
| 10b | 74% |
| 5a | 58% |

EXAMPLE 19

Mouse Carrageenan Peritoneal Inflammation Representative procedure

Inflammation is induced in mice with an intraperitoneal (IP) injection of 10 mg carrageenan in 0.5 ml of saline (Griswold et al., *Inflammation*, 13, pp. 727–739 (1989)). Drugs are administered by oral gavage in ethanol/PEG/water, β-cyclodextrin, labrosol/water or cremophor/water vehicle. The mice are sacrificed at 4 hours post carrageenan administration, then injected IP with 2 ml of saline containing 5U/ml heparin. After gentle massage of the peritoneum, a small incision is made, the contents collected and volume recorded. Samples are kept on ice until centrifuged (130×g, 8 mins at 4° C.) to remove cellular material, and the resultant supernatant stored at −20° C. IL-1β levels in the peritoneal fluid are determined by ELISA.

EXAMPLE 20

Type II Collaaen-induced Arthritis Representative procedure

Type II collagen-induced arthritis is established in male DBA/1J mice at described Wooley and Geiger (Wooley, P. H., *Methods in Enzymology*, 162, pp. 361–373 (1988) and Geiger, T., *Clinical and Experimental Rheumatology*, 11, pp. 515–522 (1993)). Chick sternum Type II collagen (4 mg/kg in 10 mM acetic acid) is emulsified with an equal volume of Freund's complete adjuvant (FCA) by repeated passages (400) between two 10 ml glass syringes with a gauge 16 double-hub needle. Mice are immunized by intradermal injection (50 1; 100 1 CII per mouse) of collagen emulsion 21 days later at the contra-lateral side of the tail base. Drugs are administered twice a day (10, 25 and 50 mg/kg) by oral gavage approximately 7 h apart. Vehicles that may be used include ethanol/PEG/water, β-cyclodextrin, labrosol/water or cremophor/water. Drug treatments are initiated within 2 h of the CII booster immunization. Inflammation is scored on a 1 to 4 scale of increasing severity on the two front paws and the scores are added to give the final score.

The data of the examples above demonstrate that compounds according to this invention display inhibitory activity towards IL-1β Converting Enzyme.

Insofar as the compounds of this invention are able to inhibit ICE in vitro and furthermore, may be delivered orally to mammals, they are of evident clinical utility for the treatment of IL-1-, apoptosis-, IGIF-, and IFN-γ-mediated diseases. These tests are predictive of the compounds ability to inhibit ICE in vivo.

While we have described a number of embodiments of this invention, it is apparent that our basic constructions may be altered to provide other embodiments which utilize the products and processes of this invention.

What is claimed is:

1. A compound represented by a formula (III):

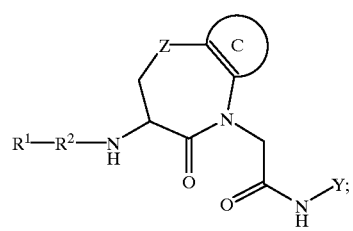

(III)

wherein

Y is:

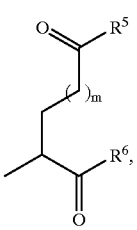

(a)

provided that when $R^5$ is —OH then Y can also be

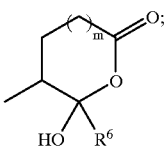

m is 0 or 1;

Z is —$CH_2$—, —C(O)—, or —C(=N—$OR^{21}$)—;

C is benzo, wherein the ring is optionally singly or multiply substituted with —$R^4$;

$R^1$ is -aryl, -heteroaryl, -alkylaryl, or -alkylheteroaryl, wherein each -aryl or -heteroaryl is optionally singly or multiply substituted with $R^{17}$;

$R^2$ is a bond, —C(O)—, —C(O)C(O)—, —S(O)$_2$—, —OC(O)—, —N(H)C(O)—, —N(H)S(O)$_2$—, —N(H)C(O)C(O)—, —CH=CHC(O)—, —OCH$_2$C(O)—, —N(H)CH$_2$C(O)—, —N($R^{19}$)C(O)—, —N($R^{19}$)S(O)$_2$—, —N($R^{19}$)C(O)C(O)—, or —N($R^{19}$)CH$_2$C(O)—;

R⁴ is —OH, —F, —Cl, —Br, —I, —NO₂, —CN, —NH₂, —CO₂H, —C(O)NH₂, —N(H)C(O)H, —N(H)C(O)NH₂, -alkyl, -cycloalkyl, -perfluoroalkyl, —O-alkyl, —N(H)alkyl, —N(alkyl)₂, —C(O)N(H)alkyl, —CON(alkyl)₂, —N(H)C(O)alkyl, —N(H)C(O)N(H)alkyl, —N(H)C(O)N(alkyl)₂, —S-alkyl, —S(O)₂alkyl, —C(O)alkyl, —CH₂NH₂, —CH₂N(H)alkyl, or —CH₂N(alkyl)₂;

R⁵ is —OH, —OR⁸, or —N(H)OH;

R⁶ is —H, —CH₂OR⁹, —CH₂SR¹⁰, —CH₂N(H)R⁹, —CH₂N(R⁹)R¹², —CHN₂, —CH₂F, —CH₂Cl, —C(O)N(R¹¹)R¹², —R¹³, or —R¹⁴;

R⁸ is -alkyl, -cycloalkyl, -aryl, -heteroaryl, -alkylaryl, -alkylheteroaryl, or -alkylheterocycle;

R⁹ is —H, —COaryl, —COheteroaryl, —COalkylaryl, —COalkylheteroaryl, -alkylaryl, -alkylheteroaryl, -aryl, -heteroaryl, or —P(O)R¹⁵R¹⁶;

R¹⁰ is -alkylaryl or -alkylheteroaryl;

R¹¹ and R¹² are independently —H, -alkyl, -aryl, -heteroaryl, -cycloalkyl, -alkylaryl, or -alkylheteroaryl;

R¹³ is -alkylaryl or -alkylheteroaryl;

R¹⁴ is

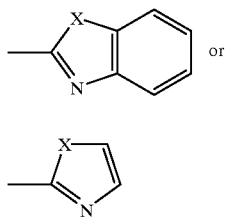

wherein (i) is optionally substituted with one or more —R¹⁷ and (ii) is optionally substituted with one or more —R¹⁷, —R¹⁸ or —R²⁰;

X is O or S;

R¹⁵ and R¹⁶ are independently —H, —OH, -alkyl, -aryl, -heteroaryl, -cycloalkyl, -alkylaryl, -alkylheteroaryl, —Oalkyl, —Oaryl, —Oheteroaryl, —Oalkylaryl, or —Oalkylheteroaryl;

R¹⁷ is —OH, —F, —Cl, —Br, —I, —NO₂, —CN, —NH₂, —CO₂H, —C(O)NH₂, —N(H)C(O)H, —N(H)C(O)NH₂, —S(O)₂NH₂, —C(O)H, -alkyl, -cycloalkyl, -perfluoroalkyl, —O-alkyl, —N(H)alkyl, —N(alkyl)₂, —CO₂alkyl, —C(O)N(H)alkyl, —C(O)N(alkyl)₂, —N(H)C(O)alkyl, —N(H)C(O)N(H)alkyl, —N(H)C(O)N(alkyl)₂, —S(O)₂N(H)alkyl, —S(O)₂N(alkyl)₂, —S-alkyl, —S(O)₂alkyl, or —C(O)alkyl;

R¹⁸ is -aryl, -heteroaryl, -alkylaryl, -alkylheteroaryl, —O-aryl, —O-heteroaryl, —O-alkylaryl, —O-alkylheteroaryl, —N(H)aryl, —N(aryl)₂, —N(H)heteroaryl, —N(heteroaryl)₂, —N(H)alkylaryl, —N(alkylaryl)₂, —N(H)alkylheteroaryl, —N(alkylheteroaryl)₂, —S-aryl, —S-heteroaryl, —S-alkylaryl, —S-alkylheteroaryl, —C(O)aryl, —C(O)heteroaryl, —C(O)alkylaryl, —C(O)alkylheteroaryl, —CO₂aryl, —CO₂heteroaryl, —CO₂alkylaryl, —CO₂alkylheteroaryl, —C(O)N(H)aryl, —C(O)N(aryl)₂, —C(O)N(H)heteroaryl, —C(O)N(heteroaryl)₂, —C(O)N(H)alkylaryl, —C(O)N(alkylaryl)₂, —C(O)N(H)alkylheteroaryl, —C(O)N(alkylheteroaryl)₂, —S(O)₂-aryl, —S(O)₂-heteroaryl, —S(O)₂-alkylaryl, —S(O)₂-alkylheteroaryl, —S(O)₂N(H)-aryl, —S(O)₂N(H)-heteroaryl, —S(O)₂N(H)-alkylaryl, —S(O)₂N(H)-alkylheteroaryl, —SO₂N(aryl)₂, —SO₂N(heteroaryl)₂, —SO₂N(alkylaryl)₂, —SO₂N(alkylheteroaryl)₂, —N(H)C(O)N(H)aryl, —N(H)C(O)N(H)heteroaryl, —N(H)C(O)N(H)alkylaryl, —N(H)C(O)N(H)alkylheteroaryl, —N(H)C(O)N(aryl)₂, —N(H)C(O)N(heteroaryl)₂, N(H)C(O)N(alkylaryl)₂, or —N(H)C(O)N(alkylheteroaryl)₂;

R¹⁹ is —H, -alkyl, -cycloalkyl, -aryl, -heteroaryl, -alkylaryl, or -alkylheteroaryl, or -alkylheterocycle;

R²⁰ is -alkyl-R¹⁸; and

R²¹ is H, alkyl, alkylaryl, or -alkylheteroaryl.

2. A compound represented by formula (III):

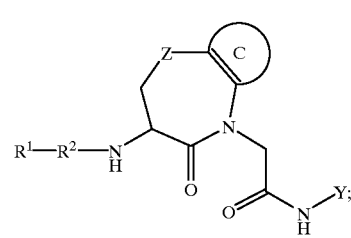

(III)

wherein Y is:

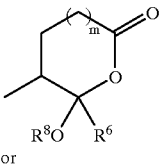

(d)

or

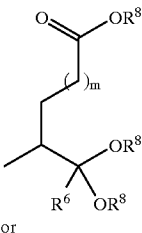

(e)

or

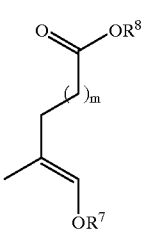

(f)

m is 0 or 1;

Z is —CH₂, —, [—O—, —S—, —S(O)—, —S(O)₂—,] —C(O)—, or —C(=N—OR²¹)—;

C is benzo, wherein the ring is optionally singly or multiply substituted with —R⁴;

R¹ is -aryl, -heteroaryl, -alkylaryl, or -alkylheteroaryl, wherein each -aryl or -heteroaryl is optionally singly or multiply substituted with R¹⁷;

R² is a bond, —C(O)—, —C(O)C(O)—, —S(O)₂—, —OC(O)—, —N(H)C(O)—, —N(H)S(O)₂—, —N(H)

C(O)C(O)—, —CH=CHC(O)—, —OCH$_2$C(O)—, —N(H)CH$_2$C(O)—, —N(R$^{19}$)C(O)—, —N(R$^{19}$)S(O)$_2$—, —N(R$^{19}$)C(O)C(O)—, or —N(R$^{19}$)CH$_2$C(O)—;

R$^4$ is —OH, —F, —Cl, —Br, —I, —NO$_2$, —CN, —NH$_2$, —CO$_2$H, —C(O)NH$_2$, —N(H)C(O)H, —N(H)C(O)NH$_2$, -alkyl, -cycloalkyl, -perfluoroalkyl, —O-alkyl, —N(H)alkyl, —N(alkyl)$_2$, —C(O)N(H)alkyl, —CON(alkyl)$_2$, —N(H)C(O)alkyl, —N(H)C(O)N(H)alkyl, —N(H)C(O)N(alkyl)$_2$, —S-alkyl, —S(O)$_2$alkyl, —C(O)alkyl, —CH$_2$NH$_2$, —CH$_2$N(H)alkyl, or —CH$_2$N(alkyl)$_2$;

R$^6$ is —H, —CH$_2$OR$^9$, —CH$_2$SR$^{10}$, —CH$_2$N(H)R$^9$, —CH$_2$N(R$^9$)R$^{12}$, —CHN$_2$, —CH$_2$F, —CH$_2$Cl, —C(O)N(R$^{11}$)R$^{12}$, —R$^{13}$, or —R$^{14}$;

R$^7$ is —C(O)alkyl, —C(O)cycloalkyl, —C(O)alkyenyl, —C(O)alkylaryl, —C(O)alkylheteroaryl, —C(O)heterocycle, or —C(O)alkylheterocycle;

R$^8$ is -alkyl, -cycloalkyl, -aryl, -heteroaryl, -alkylaryl, -alkylheteroaryl, or -alkylheterocycle;

R$^9$ is —H, —C(O)aryl, —C(O)heteroaryl, —C(O)alkylaryl, —C(O)alkylheteroaryl, -alkylaryl, -alkylheteroaryl, -aryl, -heteroaryl, or —P(O)R$^{15}$R$^{16}$;

R$^{10}$ is -alkylaryl or -alkylheteroaryl;

R$^{11}$ and R$^{12}$ are independently —H, -alkyl, -aryl, -heteroaryl, -cycloalkyl, -alkylaryl, or -alkylheteroaryl;

R$^{13}$ is -alkylaryl or -alkylheteroaryl;

R$^{14}$ is

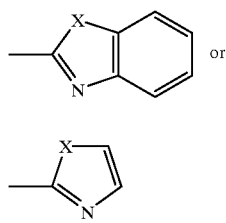

wherein (i) is optionally substituted with one or more —R$^{17}$ and (ii) is optionally substituted with one or more —R$^{17}$, —R$^{18}$ or —R$^{20}$;

X is O or S;

R$^{15}$ and R$^{16}$ are independently —H, —OH, -alkyl, -aryl, -heteroaryl, -cycloalkyl, -alkylaryl, -alkylheteroaryl, —Oalkyl, —Oaryl, —Oheteroaryl, —Oalkylaryl, or —Oalkylheteroaryl;

R$^{17}$ is —OH, —F, —Cl, —Br, —I, —NO$_2$, —CN, —NH$_2$, —CO$_2$H, —C(O)NH$_2$, —N(H)C(O)H, —N(H)C(O)NH$_2$, —S(O)$_2$NH$_2$, —C(O)H, -alkyl, -cycloalkyl, -perfluoroalkyl, —O-alkyl, —N(H)alkyl, —N(alkyl)$_2$, —CO$_2$alkyl, —C(O)N(H)alkyl, —C(O)N(alkyl)$_2$, —N(H)C(O)alkyl, —N(H)C(O)N(H)alkyl, —N(H)C(O)N(alkyl)$_2$, —S(O)$_2$N(H)alkyl, —S(O)$_2$N(alkyl)$_2$, —S-alkyl, —S(O)$_2$alkyl, or —C(O)alkyl;

R$^{18}$ is -aryl, -heteroaryl, -alkylaryl, -alkylheteroaryl, —O-aryl, —O-heteroaryl, —O-alkylaryl, —O-alkylheteroaryl, —N(H)aryl, —N(aryl)$_2$, —N(H)heteroaryl, —N(heteroaryl)$_2$, —N(H)alkylaryl, —N(alkylaryl)$_2$, —N(H)alkylheteroaryl, —N(alkylheteroaryl)$_2$, —S-aryl, —S-heteroaryl, —S-alkylaryl, —S-alkylheteroaryl, —C(O)aryl, —C(O)heteroaryl, —C(O)alkylaryl, —C(O)alkylheteroaryl, —CO$_2$aryl, —CO$_2$heteroaryl, —CO$_2$alkylaryl, —CO$_2$alkylheteroaryl, —C(O)N(H)aryl, —C(O)N(aryl)$_2$, —C(O)N(H)heteroaryl, —C(O)N(heteroaryl)$_2$, —C(O)N(H)alkylaryl, —C(O)N(alkylaryl)$_2$, —C(O)N(H)alkylheteroaryl, —C(O)N(alkylheteroaryl)$_2$, —S(O)$_2$-aryl, —S(O)$_2$-heteroaryl, —S(O)$_2$-alkylaryl, —S(O)$_2$-alkylheteroaryl, —S(O)$_2$N(H)-aryl, —S(O)$_2$N(H)-heteroaryl, —S(O)$_2$N(H)-alkylaryl, —S(O)$_2$N(H)-alkylheteroaryl, —SO$_2$N(aryl)$_2$, —SO$_2$N(heteroaryl)$_2$, —SO$_2$N(alkylaryl)$_2$, —SO$_2$N(alkylheteroaryl)$_2$, —N(H)C(O)N(H)aryl, —N(H)C(O)N(H)heteroaryl, —N(H)C(O)N(H)alkylaryl, —N(H)C(O)N(H)alkylheteroaryl, —N(H)C(O)N(aryl)$_2$, —N(H)C(O)N(heteroaryl)$_2$, N(H)C(O)N(alkylaryl)$_2$, or —N(H)C(O)N(alkylheteroaryl)$_2$;

R$^{19}$ is —H, -alkyl, -cycloalkyl, -aryl, -heteroaryl, -alkylaryl, or -alkylheteroaryl, or -alkylheterocycle;

R$^{20}$ is -alkyl-R$^{18}$; and

R$^{21}$ is H, alkyl, alkylaryl, or -alkylheteroaryl.

3. The compound according to claims 1 or 2, wherein:

m is 0;

C is benzo, wherein the C ring is optionally singly or multiply substituted with —R$^4$;

R$^1$ is phenyl, naphthyl, or isoquinolinyl, each optionally singly or multiply substituted with R$^{17}$, wherein R$^{17}$ is —OH, —NH$_2$, —Cl, —F, —Oalkyl, or —N(alkyl)$_2$;

R$^2$ is —C(O)—, —S(O)$_2$—, —C(O)C(O)— or —CH$_2$C(O)—;

R$^4$ is fluoro or chloro;

R$^6$ is —H or —R$^{14}$ wherein X is O and for formula (i) R$^{17}$ is —Oalkyl, —F or —Cl and for formula (ii) R$^{18}$ is aryl wherein aryl is phenyl;

R$^8$ is methyl, ethyl, n-propyl, isopropyl, cyclopentyl, phenethyl, or benzyl; and R$^9$ is —C(O)aryl, —C(O)heteroaryl, —C(O)alkylaryl, —C(O)alkylheteroaryl, -alkylaryl, -alkylheteroaryl, -aryl, or -heteroaryl.

4. The compound according to claim 3 wherein C is benzo and R$^6$ is H.

5. The compound according to claim 1 wherein R$^5$ is —OH.

6. The compound according to claim 2 wherein R$^7$ is —C(O)alkyl.

7. The compound according to claims 1 or 2, wherein Z is —C(O)—.

8. A pharmaceutical composition comprising: a) a compound according to any one of claims and b) a pharmaceutical accepatable carrier, adjuvant or vehicle.

9. A method for treating a disease selected from an inflammatory disease, osteoarthritis, glomerulonephritis, rheumatoid arthritis, psoriasis, graft vs host disease, sepsis, or septic shock in a patient comprising the step of administering to said patient a pharmaceutical composition according to claim 8.

10. The method according to claim 9, wherein the disease is osteoarthritis, rheumatoid arthritis, or psoriasis.

11. A process for preparing a compound represented by formula (V):

(V)

wherein:

$R^{22}$ is:

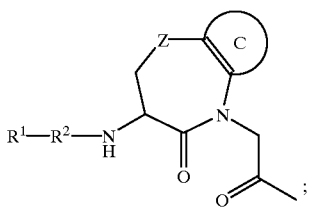

$R^{23}$ is:

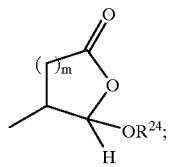 (a)

m is 1 or 2;
Z is —CH$_2$—, [—O—, —S—, —S(O)—, —S(O)$_2$—,] —C(O)—, or —C (=N—OR$^{21}$)—;
C is benzo, wherein the ring is optionally singly or multiply substituted with —R$^4$;
R$^1$ is -aryl, -heteroaryl, -alkylaryl, or -alkylheteroaryl, wherein each -aryl or -heteroaryl is optionally singly or multiply substituted with R$^{17}$;
R$^2$ is a bond, —C(O)—, —C(O)C(O)—, —S(O)$_2$—, —OC(O)—, —N(H)C(O)—, —N(H)S(O)$_2$—, —N(H)C(O)C(O)—, —CH=CHC(O)—, —OCH$_2$C(O)—, —N(H)CH$_2$C(O)—, —N(R$^{19}$)C(O)—, —N(R$^{19}$)S(O)$_2$—, —N(R$^{19}$)C(O)C(O)—, or —N(R$^{19}$)CH$_2$C(O)—;
R$^4$ is —OH, —F, —Cl, —Br, —I, —NO$_2$, —CN, —NH$_2$, —CO$_2$H, —C(O)NH$_2$, —N(H)C(O)H, —N(H)C(O)NH$_2$, -alkyl, -cycloalkyl, -perfluoroalkyl, —O-alkyl, —N(H)alkyl, —N(alkyl)$_2$, —C(O)N(H)alkyl, —CON(alkyl)$_2$, —N(H)C(O)alkyl, —N(H)C(O)N(H)alkyl, —N(H)C(O)N(alkyl)$_2$, —S-alkyl, —S(O)$_2$alkyl, —C(O)alkyl, —CH$_2$NH$_2$, —CH$_2$N(H)alkyl, or —CH$_2$N(alkyl)$_2$;
R$^{19}$ is —H, -alkyl, -cycloalkyl, -aryl, -heteroaryl, -alkylaryl, or -alkylheteroaryl, or -alkylheterocycle;
R$^{21}$ is H, alkyl, alkylaryl, or alkylheteroaryl; and
R$^{24}$ -alkyl, -cycloalkyl, -aryl, -heteroaryl, -alkylaryl, or -alkylheteroaryl, or -alkylheterocycle; comprising the steps of:

a) reacting a compound represented by formula (VI):
(VI) R$^{22}$—OH, wherein R$^{22}$ is as defined above, with a compound represented by formula (VII):

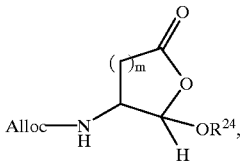

wherein R$^{24}$ is as defined above, in the presence of an inert solvent, triphenylphoshine, a nucleophilic scavenger, and tetrakis-triphenyl phosphine palladium(0) at ambient temperature under an inert atmosphere; and
b) adding to the mixture formed in step a), HOBT and EDC.

12. The process according to claim 11, wherein:
C is benzo, wherein any hydrogen bound to any ring atom is optionally replaced by R$^4$;
R$^1$ is phenyl, naphthyl, or isoquinolinyl, each optionally singly or multiply substituted with R$^{17}$, wherein R$^{17}$ is —OH, —NH$_2$, —Cl, —F, —Oalkyl, or —N(alkyl)$_2$;
R$^2$ is —C(O)—, —S(O)$_2$—, —C(O)C(O)—, or —CH$_2$C(O)—;
R$^4$ is fluoro or chloro; and
m is 1.

13. The process according to claim 12, wherein:
C is benzo, wherein any hydrogen bound to any ring atom is optionally replaced by R$^4$; and
R$^6$ is H.

14. The process according to claim 12 wherein the inert solvent is CH$_2$Cl$_2$, DMF, or a mixture of CH$_2$Cl$_2$ and DMF.

15. The process according to any one of claims 12 or 13, wherein the nucleophilic scavenger is dimedone, morpholine, or dimethyl barbituric acid.

16. The process according to claim 14, wherein the nucleophilic scavenger is dimethyl barbituric acid.

17. The process according to claim 14, wherein the inert solvent is CH$_2$Cl$_2$, DMF, or a mixture of CH$_2$Cl$_{12}$ and DMF.

18. The process according to claim 17, wherein the nucleophilic scavenger is dimethyl barbituric acid.

* * * * *